US010765301B2

(12) United States Patent
Dejima

(10) Patent No.: US 10,765,301 B2
(45) Date of Patent: Sep. 8, 2020

(54) SURGICAL APPARATUS FOR ENDOSCOPE AND EXTERIOR TUBE

(71) Applicant: FUJIFILM Corporation, Tokyo (JP)

(72) Inventor: Takumi Dejima, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 406 days.

(21) Appl. No.: 15/470,915

(22) Filed: Mar. 28, 2017

(65) Prior Publication Data

US 2017/0196439 A1    Jul. 13, 2017

Related U.S. Application Data

(63) Continuation of application No. PCT/JP2015/077586, filed on Sep. 29, 2015.
(Continued)

(51) Int. Cl.
*A61B 1/00* (2006.01)
*A61B 17/34* (2006.01)
(Continued)

(52) U.S. Cl.
CPC ...... *A61B 1/00135* (2013.01); *A61B 1/00075* (2013.01); *A61B 1/00128* (2013.01);
(Continued)

(58) Field of Classification Search
CPC ............ A61B 1/00075; A61B 1/00135; A61B 1/00154; A61B 1/015
See application file for complete search history.

(56) References Cited

U.S. PATENT DOCUMENTS 5,025,778 A * 6/1991 Silverstein ......... A61B 1/00078
600/104
5,575,756 A * 11/1996 Karasawa .......... A61B 1/00068
600/121
(Continued)

FOREIGN PATENT DOCUMENTS

JP    H09276287    10/1997
JP    2004180858    7/2004
(Continued)

OTHER PUBLICATIONS

"Office Action of Europe Counterpart Application," dated Dec. 13, 2018, p. 1-p. 5.
(Continued)

*Primary Examiner* — Aaron B Fairchild
(74) *Attorney, Agent, or Firm* — JCIPRNET

(57) ABSTRACT

Provided are a surgical apparatus for an endoscope and an exterior tube that can supply a pneumoperitoneum gas into a body cavity without causing degradation of operability. An exterior tube is sheathed to an outer tube insertion part of an outer tube that is inserted into a body cavity through a body wall and guides an endoscope and a treatment tool into the body cavity, and an outer peripheral surface of the exterior tube is provided with a locking part that restricts the forward and backward movement of the exterior tube with respect to the body wall and the rotation of the exterior tube around an axis. A gap between an inner peripheral surface of the exterior tube and an outer peripheral surface of the outer tube insertion part is used as an air supply passage for supplying the pneumoperitoneum gas within the body cavity.

3 Claims, 23 Drawing Sheets

Related U.S. Application Data

(60) Provisional application No. 62/057,476, filed on Sep. 30, 2014.

(51) Int. Cl.
*A61B 1/015* (2006.01)
*A61B 1/018* (2006.01)
*A61B 1/313* (2006.01)

(52) U.S. Cl.
CPC ...... *A61B 1/00133* (2013.01); *A61B 1/00154* (2013.01); *A61B 1/015* (2013.01); *A61B 1/018* (2013.01); *A61B 1/3132* (2013.01); *A61B 17/34* (2013.01); *A61B 17/3415* (2013.01)

(56) References Cited

U.S. PATENT DOCUMENTS

2007/0203393 A1* 8/2007 Stefanchik ......... A61B 1/00073
600/106
2010/0010298 A1 1/2010 Bakos et al.
2015/0080650 A1 3/2015 Dejima et al.

FOREIGN PATENT DOCUMENTS

JP 2014018563 2/2014
WO 2013176167 11/2013

OTHER PUBLICATIONS

"International Search Report (Form PCT/ISA/210)", dated Dec. 22, 2015, with English translation thereof, pp. 1-2.

"Written Opinion (Form PCT/ISA/237)", dated Dec. 22, 2015, with English translation thereof, pp. 1-6.

"Office Action of European Counterpart Application," dated Jun. 7, 2018, pp. 1-3.

"Search Report of Euorpe Counterpart Application", dated Oct. 20, 2017, p. 1-p. 7, in which the listed references were cited.

* cited by examiner

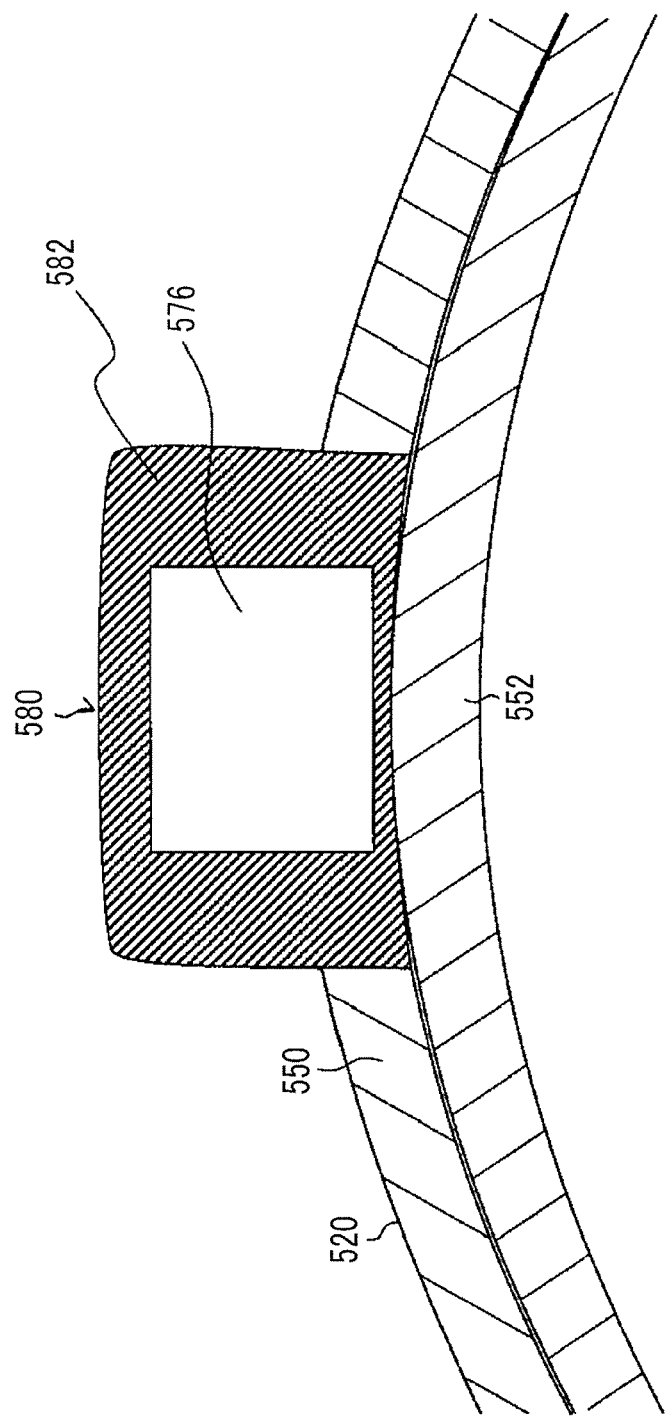

SURGICAL APPARATUS FOR ENDOSCOPE AND EXTERIOR TUBE

CROSS-REFERENCE TO RELATED APPLICATIONS

This application is a Continuation of PCT International Application No. PCT/JP2015/077586 filed on Sep. 29, 2015, which claims priority under 35 U.S.C. § 119(a) to U.S. Provisional Application No. 62/057,476 filed on Sep. 30, 2014. Each of the above applications is hereby expressly incorporated by reference, in their entirety, into the present application.

BACKGROUND OF THE INVENTION

1. Field of the Invention

The present invention relates to a surgical apparatus for an endoscope and an exterior tube, and particularly, relates to a surgical apparatus for an endoscope provided with an exterior tube sheathed to an outer tube that guides an insertion part of a medical instrument into a body cavity, and an exterior tube.

2. Description of the Related Art

In recent years, since invasion to a patient is small compared to surgery in which a laparotomy, a thoracotomy, or the like, is performed, endoscopic surgery using endoscopes (hard endoscopes), such as a laparoscope, is widely performed. In the endoscopic surgery, a plurality of holes are made in a patient's body wall, an endoscope is inserted into a body cavity from one hole of them, and a treatment tool is inserted into the body cavity from another hole. Then, treatment of a living body tissue is performed with the treatment tool while observing the living body tissue within the body cavity with the endoscope.

Generally, in the endoscopic surgery, one or a plurality of treatment tools are used simultaneously with the endoscope. Therefore, since it is difficult for one operator to simultaneously operate the endoscope and the plurality of treatment tools, for example, a task where the operator operates treatment tools using both hands while making an assistant called an endoscopic technician operate the endoscope is normally performed.

In this way, in the endoscopic surgery, it is general that the operator's hands are bound by the operation of the treatment tool, and the operation of the endoscope is performed by the assistant. Therefore, in a case where the observation position of the endoscope is changed, the operator should serially give instructions to the assistant. Hence, the task of correctly directing the orientation of the endoscope to a direction desired by the operator is difficult, and stress is likely to be imposed on the operator. Additionally, since the assistant performs an operation after the operator issues an instruction, there is a tendency that surgery time is likely to be prolonged. Additionally, the assistant should operate the endoscope so as not to interfere with an operator's procedure, and the operation is likely to become complicated.

In contrast, the applicant of the present application suggests a technique in which an endoscope and a treatment tool are combined together by an outer tube, and if the treatment tool is moved forward and backward, the endoscope is also moved forward and backward in an interlocking manner with this movement of the treatment tool (refer to WO2013/176167A). Specifically, the outer tube that guides an insertion part of the endoscope and an insertion part of the treatment tool into a body cavity includes a tubular outer tube body that is inserted in a state where the insertion part of the endoscope and the insertion part of the treatment tool are made to be parallel to each other. An interlocking member that is movable forward and backward in an axial direction and has an endoscope-coupling part and a treatment tool-coupling part is provided inside the outer tube body. The insertion part of the endoscope and the insertion part of the treatment tool are held by the respective coupling parts of the interlocking member in a state where the insertion parts are made to be parallel to each other. If the insertion part of the treatment tool is moved in the axial direction, the insertion part of the endoscope also moves in the axial direction in an interlocking manner with this movement. Accordingly, the number of the holes made in the patient's body wall can be reduced, the invasion to the patient can be suppressed, and the visual field of the endoscope can be easily changed while an operator operates the treatment tool without asking for an assistant's help.

Additionally, an outer tube that enables a pneumoperitoneum gas to be supplied into a body cavity through an insertion passage through which an endoscope or a treatment tool are inserted is disclosed in JP1997-276287A (JP-H09-276287A).

SUMMARY OF THE INVENTION

However, if the outer tube suggested in WO2013/176167A by the applicant of the present application is provided with an air supply tube connecting part for supply of a pneumoperitoneum gas as in JP1997-276287A (JP-H09-276287A), an air supply tube connected to the air supply tube connecting part, and an endoscope or a treatment tool inserted through the outer tube tend to contact each other. For that reason, it is necessary to perform such operation that any twist between the air supply tube and the endoscope or the treatment tool is avoided so that neither clogging of the air supply tube nor the malfunction of the endoscope or the treatment tool occurs, and therefore degradation of operability may be caused. Particularly, in the outer tube of WO2013/176167A, the arrangement between the endoscope and the treatment tool is adjusted by rotating the outer tube around an axis. Even that case, any twist between the air supply tube and the endoscope or treatment tool may occur, and therefore degradation of operability may be made remarkable.

The invention has been made in view of such circumstances and an object thereof is to provide a surgical apparatus for an endoscope and an exterior tube that can supply a pneumoperitoneum gas into a body cavity without causing degradation of operability.

In order to achieve the above object, a surgical apparatus for an endoscope according to an aspect of the invention is a surgical apparatus for an endoscope comprising an outer tube that guides an insertion part of a medical instrument into a body cavity; and an exterior tube to be sheathed to the outer tube. The exterior tube includes an exterior tube main body having a base end, a distal end, and a longitudinal axis, a distal end opening provided at the distal end of the exterior tube main body, a base end opening provided at the base end of the exterior tube main body, an insertion passage that is provided along the longitudinal axis of the exterior tube main body, and allows the distal end opening and the base end opening to communicate with each other and the outer tube to be inserted therethrough, a locking part that has a recess or protrusion formed along the longitudinal axis in an outer peripheral surface of the exterior tube main body and prevents the rotation of the exterior tube main body about the longitudinal axis, a supply port opening to a base end side of the exterior tube main body, an air supply port opening to a distal end side of the exterior tube main body, and an air supply passage that is formed along the longitudinal axis of the exterior tube main body and allows the supply port and the air supply port to communicate with each other.

According to this aspect, the locking part provided in the exterior tube prevents the outer tube from unintentionally rotating around the axis with respect to a body wall during the operation of the medical instrument, or the like. Also, by providing the air supply passage and the supply port for a pneumoperitoneum gas along the longitudinal axis of the exterior tube main body of the exterior tube, any contact between the air supply tube connected to the supply port and the medical instrument inserted through the outer tube can be easily avoided. Therefore, any twist between the air supply tube and the medical instrument can be prevented in advance without paying special attention. Hence, degradation of the operability for avoiding the twist between the air supply tube and the medical instrument does not occur, either.

Additionally, regardless of the presence/absence of insertion of the medical instrument into the outer tube, an air-supply flow rate in the air supply passage can be substantially kept constant, and stable supply of the pneumoperitoneum gas into the body cavity can be performed.

In the surgical apparatus for an endoscope according to the aspect of the invention, it is possible to adopt an aspect in which the air supply passage is provided inside an outer peripheral wall of the exterior tube main body along the locking part.

According to this aspect, the air supply passage can be formed without causing an increase in the size of the exterior tube by making the locking part of the exterior tube serve also as an air supply tube that forms the air supply passage.

In the surgical apparatus for an endoscope according to the aspect of the invention, it is possible to adopt an aspect in which the surgical apparatus for an endoscope further comprises an air supply tube that is provided in contact with the outer peripheral surface of the exterior tube main body, and the air supply tube has the air supply passage and functions as the locking part.

According to this aspect, the air supply passage can be formed without causing an increase in the size of the exterior tube by making the air supply tube forming the air supply passage serve also as the locking part of the exterior tube.

In the surgical apparatus for an endoscope according to the aspect of the invention, it is possible to adopt an aspect in which the air supply passage is constituted by a gap formed between an inner peripheral surface of the exterior tube main body and an outer peripheral surface of the outer tube.

According to this aspect, since it is unnecessary to provide the air supply passage inside the outer peripheral wall of the exterior tube, or the like, the air supply passage can be provided with a simple configuration. Additionally, since the air supply passage is formed along the outer peripheral surface of the outer tube, the cross-sectional area of the air supply passage is large so that a large air-supply flow rate can be obtained.

In the surgical apparatus for an endoscope according to the aspect of the invention, it is possible to adopt an aspect in which the surgical apparatus for an endoscope further comprises an airtight holding member that is provided inside the base end side of the exterior tube main body and holds airtightness in contact with the outer peripheral surface of the outer tube inserted through the insertion passage, and the supply port is provided closer to the distal end side than the airtight holding member with respect to the longitudinal axis of the exterior tube main body.

According to this aspect, the pneumoperitoneum gas can be prevented from leaking to the outside of a body via a gap between the inner peripheral surface of the exterior tube main body and the outer peripheral surface of the outer tube.

In the surgical apparatus for an endoscope according to the aspect of the invention, it is possible to adopt an aspect in which the outer tube includes an outer tube body having a distal end, a base end, and a longitudinal axis, a first distal end opening and a second distal end opening provided at the distal end of the outer tube body, a first base end opening and a second base end opening provided at the base end of the outer tube body, a first insertion passage that is provided along the longitudinal axis of the outer tube body, and allows the first distal end opening and the first base end opening to communicate with each other and a first medical instrument to be inserted therethrough so as to be movable forward and backward, a second insertion passage that is provided along the longitudinal axis of the outer tube body, allows the second distal end opening and the second base end opening to communicate with each other, and has a second medical instrument inserted therethrough to be movable forward and backward, and an interlocking member that has a first coupling part to be coupled to the first medical instrument inserted through the first insertion passage and a second coupling part to be coupled to the second medical instrument inserted through the second insertion passage, and is movable forward and backward inside the outer tube body.

According to this aspect, since any one of the first medical instrument and the second medical instrument can be moved forward and backward by being interlocked with the forward and backward movement of the other of the first medical instrument and the second medical instrument, the operation of the medical instruments by one operator is allowed.

In the surgical apparatus for an endoscope according to the aspect of the invention, it is possible to adopt an aspect in which the interlocking member has a non-sensing region where the forward and backward movement of any one of the first medical instrument and the second medical instrument does not interlock with the forward and backward movement of the other of the first medical instrument and the second medical instrument, and a sensing region where the forward and backward movement of any one of the first medical instrument and the second medical instrument interlocks with the forward and backward movement of the other of the first medical instrument and the second medical instrument.

According to this aspect, for example, since any one of the first medical instrument and the second medical instrument can be made not to interlock with minute forward and backward movement of the other thereof, and operability can be improved.

An exterior tube according to another aspect of the invention is an exterior tube to be used for an outer tube that guides an insertion part of a medical instrument into a body cavity. The exterior tube comprises an exterior tube main body having a base end, a distal end, and a longitudinal axis; a distal end opening provided at the distal end of the exterior tube main body; a base end opening provided at the base end of the exterior tube main body; an insertion passage that is provided along the longitudinal axis of the exterior tube main body, and allows the distal end opening and the base end opening to communicate with each other, and the outer tube, which guides the insertion part of the medical instrument into the body cavity, to be inserted therethrough; a locking part that has a recess or protrusion formed along the longitudinal axis in an outer peripheral surface of the exterior tube main body and prevents the rotation of the exterior tube main body about the longitudinal axis; a supply port opening to a base end side of the exterior tube main body; an air supply port opening to a distal end side of the exterior tube main body; and an air supply passage that is formed along the longitudinal axis of the exterior tube main body and allows the supply port and the air supply port to communicate with each other.

According to this aspect, the locking part provided in the exterior tube prevents the outer tube from unintentionally rotating around the axis with respect to a body wall during the operation of the medical instrument, or the like. Also, by providing the air supply passage and the supply port for a pneumoperitoneum gas along the longitudinal axis of the exterior tube main body of the exterior tube, any contact between the air supply tube connected to the supply port and the medical instrument inserted through the outer tube can be easily avoided. Accordingly, any twist between the air supply tube and the medical instrument can be prevented in advance without paying special attention. Hence, degradation of the operability for avoiding the twist between the air supply tube and the medical instrument does not occur, either.

Additionally, regardless of the presence/absence of insertion of the medical instrument into the outer tube, an air-supply flow rate in the air supply passage can be substantially kept constant, and stable supply of the pneumoperitoneum gas into the body cavity can be performed.

In the exterior tube according to the other aspect of the invention, it is possible to adopt an aspect in which the air supply passage is provided inside an outer peripheral wall of the exterior tube main body along the locking part.

According to this aspect, the air supply passage can be formed without causing an increase in the size of the exterior tube by making the locking part of the exterior tube serve also as an air supply tube that forms the air supply passage.

In the exterior tube according to the other aspect of the invention, it is possible to adopt an aspect in which the exterior tube further comprises an air supply tube that is provided in contact with the outer peripheral surface of the exterior tube main body, and the air supply tube has the air supply passage and functions as the locking part.

According to this aspect, the air supply passage can be formed without causing an increase in the size of the exterior tube by making the air supply tube forming the air supply passage serve also as the locking part of the exterior tube.

In the exterior tube according to the other aspect of the invention, it is possible to adopt an aspect in which the exterior tube further comprises an airtight holding member that is provided inside the base end side of the exterior tube main body and holds airtightness in contact with an outer peripheral surface of the outer tube inserted through the insertion passage, and the supply port is provided closer to the distal end side than the airtight holding member with respect to the longitudinal axis of the exterior tube main body.

According to this aspect, the pneumoperitoneum gas is prevented from leaking to the outside of a body via a gap between the inner peripheral surface of the exterior tube main body and the outer peripheral surface of the outer tube.

According to the invention, a pneumoperitoneum gas can be supplied into a body cavity without causing degradation of operability.

BRIEF DESCRIPTION OF THE DRAWINGS

FIG. 24 is a cross sectional view around the protrusion in the exterior tube of the other embodiment of FIG. 21, and is a view illustrating a form different from FIG. 23.

DESCRIPTION OF THE PREFERRED EMBODIMENTS

Preferred embodiments of the invention will be described below in detail according to the accompanying drawings. In addition, any of the drawings may illustrate main parts in an exaggerated manner for description, and may have dimensions different from actual dimensions.

Figure 1:
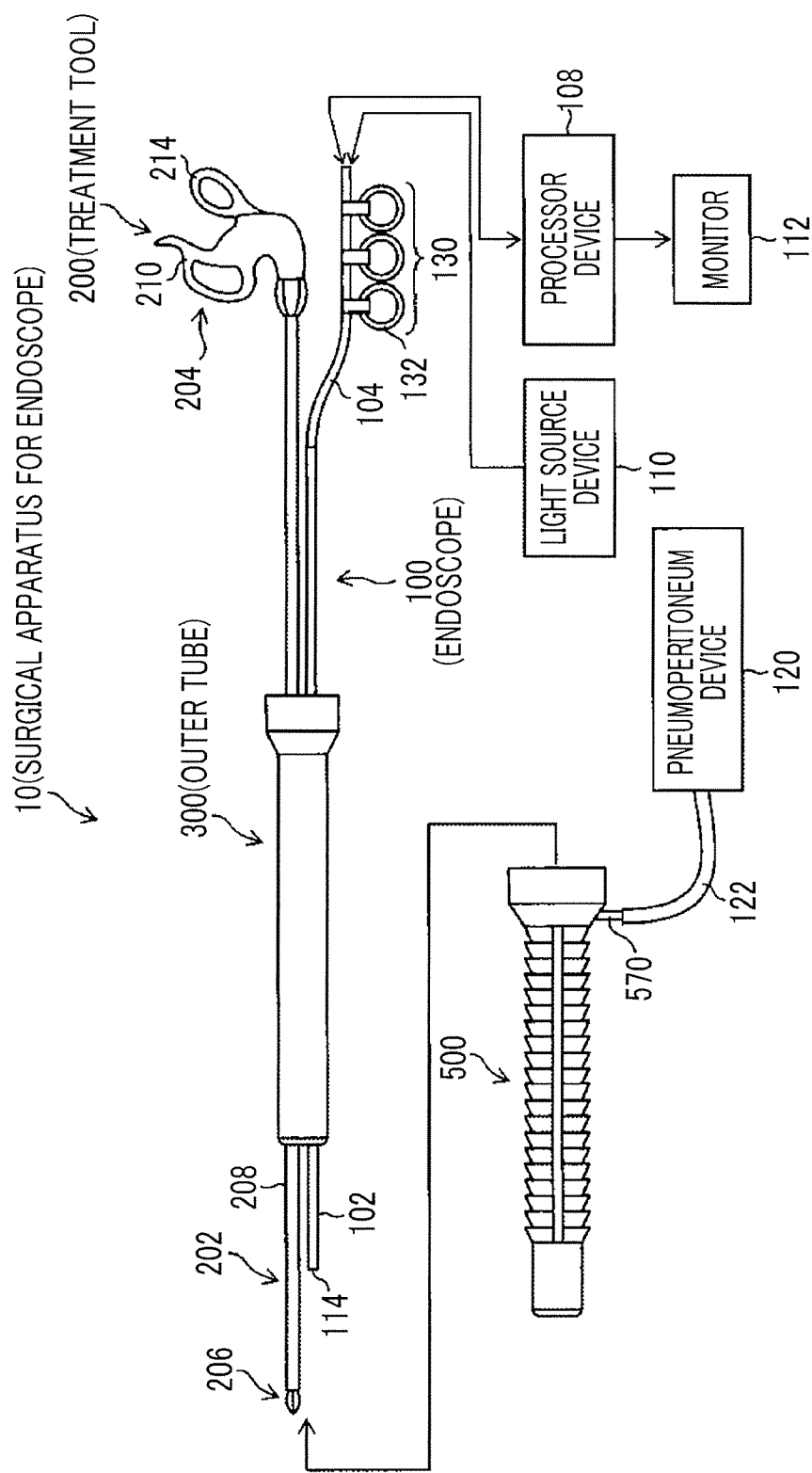
FIG. 1 is a schematic block diagram of a surgical apparatus for an endoscope according to the invention.

FIG. 1 is a schematic block diagram of a surgical apparatus for an endoscope according to the invention. As illustrated in FIG. 1, a surgical apparatus for an endoscope 10 includes an endoscope 100 that observes the inside of a patient's body cavity, a treatment tool 200 for examining or treating a diseased site within the patient's body cavity, an outer tube 300 that is inserted into a body wall and guides the endoscope 100 and the treatment tool 200 into the body cavity, and an exterior tube 500 fitted to the outer tube 300.

The endoscope 100 is, for example, a hard endoscope, such as a laparoscope, and includes an insertion part 102 (hereinafter referred to as "endoscope insertion part 102") that is inserted into a body cavity, and that has an outer peripheral part surrounded by an elongated hard tubular body, and a cable part 104 that is provided continuously with a base end side of the endoscope insertion part 102 and that has an outer peripheral part surrounded by an elongated flexible tubular body.

The cable part 104 indicates a flexible cable portion in which a wire rod, such as a cable or a light guide, which extends from a base end of the endoscope insertion part 102, is housed by covering the wire rod with, for example, a flexible insulating member, such as polyvinyl chloride.

A connector (not illustrated) is provided at an end of the cable part 104 on its extension destination, and each of a processor device 108 and a light source device 110 is detachably connected to the cable part via the connector. Additionally, the processor device 108 is connected to a monitor 112 via a cable.

Figure 2:
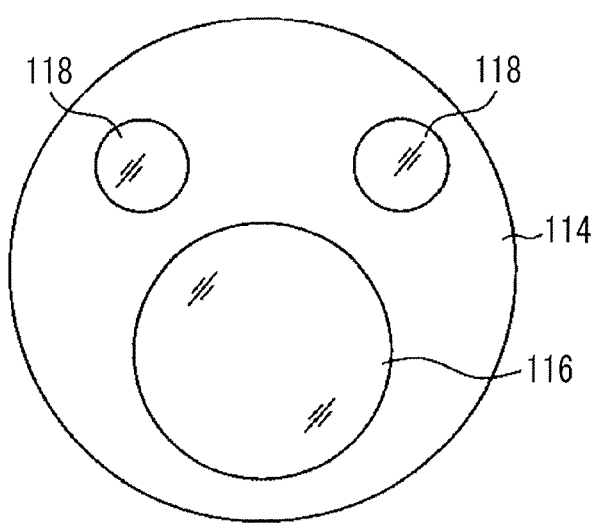
FIG. 2 is a plan view illustrating a distal end surface of an endoscope insertion part.

As illustrated in FIG. 2, a distal end surface 114 of the endoscope insertion part 102 is provided with an observation window 116 and illumination windows 118 and 118.

The observation window 116 is a constituent element of an observation part of the endoscope 100, and an objective lens of an observation optical system, and a solid image pickup element, such as a charge coupled device (CCD) image sensor or a complementary metal oxide semiconductor (CMOS) image sensor, which is disposed at an image pickup position of the objective lens, are disposed behind the observation window 116. A signal cable (not illustrated) connected to this solid image pickup element is inserted through the endoscope insertion part 102 and the cable part 104 of FIG. 1, is provided to extend up to the connector (not illustrated), and is connected to the processor device 108. An observation image picked up from the observation window 116 is formed on a light-receiving surface of the image pickup element, and is converted into electrical signals (image pickup signals), and the electrical signals are output to the processor device 108 via the signal cable and are converted into video signals. Then, the video signals are output to the monitor 112 connected to the processor device 108, and the observation image (endoscopic image) is displayed on a screen of the monitor 112.

An exit end of the light guide (not illustrated) is disposed behind the illumination windows 118 and 118 of FIG. 2. The light guide is inserted through the endoscope insertion part 102 and the cable part 104 of FIG. 1 and has an incident end disposed within the connector (not illustrated). Hence, by coupling the connector to the light source device 110, the illumination light radiated from the light source device 110 is transmitted to the illumination windows 118 and 118 via the light guide, and is radiated forward from the illumination windows 118 and 118. In addition, in FIG. 2, the two illumination windows 118 and 118 are disposed on the distal end surface 114 of the endoscope insertion part 102. However, the number of illumination windows 118 is not limited, and the number thereof may be one or may be three or more.

Addition, as illustrated in FIG. 1, the cable part 104 of the endoscope 100 is provided with a forward and backward movement operating part 130 for hooking the index finger of a right hand gripping an operating part 204 of the treatment tool 200, and performing a forward and backward movement operation of the endoscope 100 in a forward-backward direction of the endoscope 100.

The forward and backward movement operating part 130 is disposed at a position adjacent to the operating part 204 of the treatment tool 200, and has, for example, three hooking parts 132 of the same configuration. Each hooking part 132 is formed in an annular shape (ring shape) using elastic materials (for example, rubber materials), and has an opening of such a size that an index finger can pass therethrough.

Accordingly, an operator can pass the index finger of his/her right hand gripping the operating part 204 of the treatment tool 200, through any hooking part 132 of the forward and backward movement operating part 130 to perform the forward and backward movement operation of the endoscope 100, and can easily perform the operation of the treatment tool 200 and the forward and backward movement operation of the endoscope 100 only with his/her right hand. In addition, the endoscope 100 may not include the forward and backward movement operating part 130, and the detailed description of the forward and backward movement operating part 130 will be omitted.

As illustrated in FIG. 1, the treatment tool 200 consists of, for example, forceps, and includes an elongated insertion part 202 (hereinafter referred to as a "treatment tool insertion part 202") that is inserted into a body cavity, an operating part 204 that is provided on the base end side of the treatment tool insertion part 202 and is gripped by an operator, and a treatment part 206 that is provided on a distal end side of the treatment tool insertion part 202 and is operable by the operation of the operating part 204.

The treatment tool insertion part 202 is provided with a tubular sheath 208, and an operating shaft (not illustrated) that is inserted into the sheath 208 so as to be movable in the direction of an axial center. Moreover, the operating part 204 is provided with a fixed handle 210, and a movable handle 214 that is turnably coupled to the fixed handle 210 via a turning pin. A base end part of the operating shaft is coupled to the movable handle 214.

The treatment part 206 is provided with a pair of gripping members that is openable and closable. The gripping members are coupled to a distal end part of the operating shaft via a driving mechanism (not illustrated). With the turning operation of the movable handle 214 of the operating part 204, the gripping members of the treatment part 206 are opened and closed via the operating shaft and the driving mechanism.

In addition, the treatment tool 200 is not limited to the forceps, and may be, for example, other treatment tools, such as a laser probe, a suture device, an electric scalpel, a needle holder, an ultrasonic device, and an aspirator.

As illustrated in FIG. 1, the outer tube 300 allows the endoscope insertion part 102 and the treatment tool insertion part 202, which are inserted thereinto from the base end side, to be inserted therethrough and delivered from the distal end side. By inserting the outer tube 300 into a body wall and having a base end side thereof disposed outside of the body and a distal end side thereof disposed within the body cavity, the endoscope insertion part 102 and the treatment tool insertion part 202 are guided into the body cavity with one outer tube 300. Additionally, the outer tube 300 includes an interlocking function of moving the endoscope insertion part 102 and the treatment tool insertion part 202 forward and backward in an interlocking manner as will be described below in detail. Accordingly, for example, the endoscope insertion part 102 can also be moved forward and backward by the forward and backward movement operation of only the treatment tool insertion part 202, and a suitable observation image can be obtained without performing the forward and backward movement operation of the endoscope insertion part 102. The details of the configuration and working of the outer tube 300 will be described below.

Figure 3:
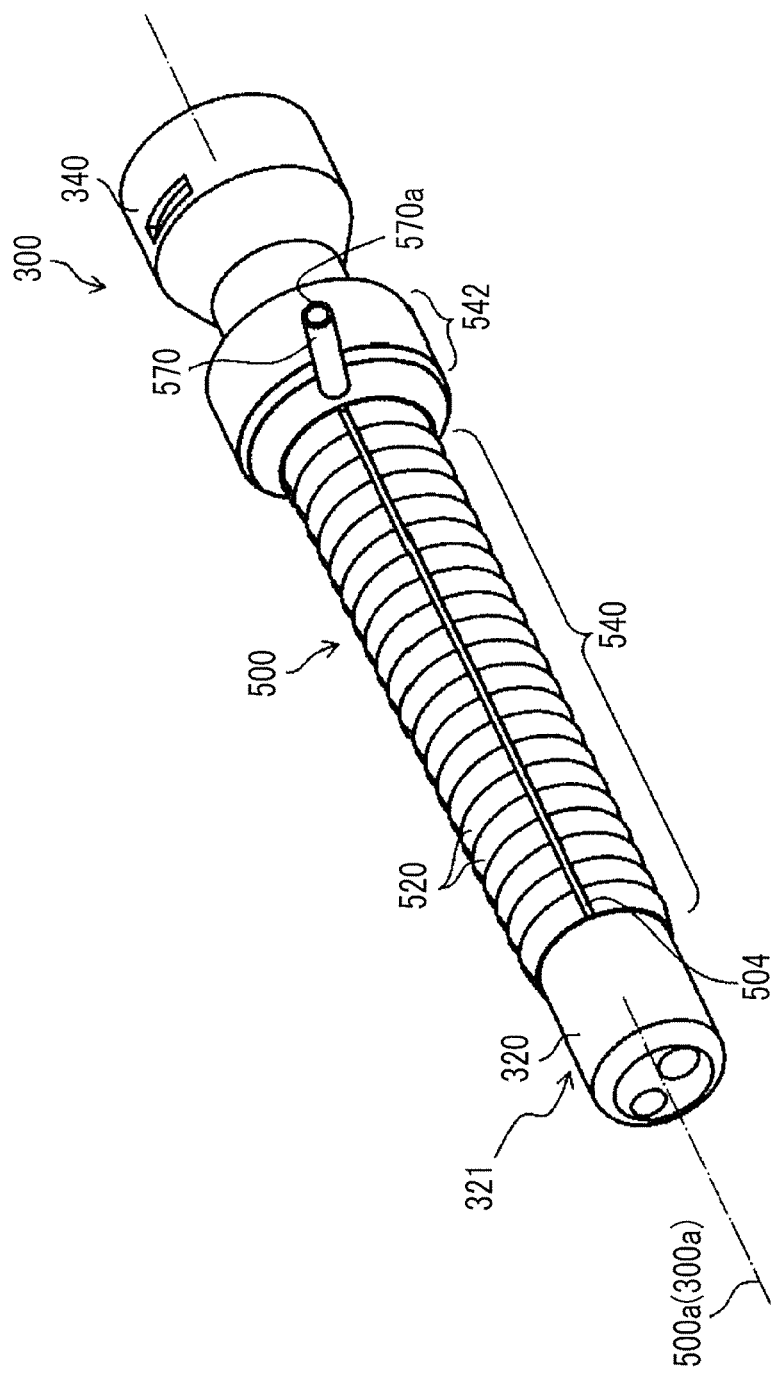
FIG. 3 is a perspective view illustrating a state where an exterior tube is fitted to an outer tube.

The exterior tube 500 illustrated in FIG. 1 is formed in a tubular shape, and as illustrated in FIG. 3, is externally fitted (sheathed) to and fixed to an outer peripheral surface of the outer tube 300 (a long tubular outer tube body 320 to be described below). Although detailed description is omitted, an outer peripheral part of the exterior tube 500 is provided with a number of lateral grooves 520 running along in a circumferential direction, and longitudinal grooves 504 running along an axial direction are provided, for example, in four places in the circumferential direction.

Accordingly, in a state where the outer tube 300 is inserted into a body wall together with the exterior tube 500, a number of the lateral grooves 520 of the exterior tube 500 restrict the forward and backward movement of the exterior tube 500 with respect to the body wall, and the longitudinal grooves in four places of the exterior tube 500 restrict the rotation of the exterior tube 500 in the circumferential direction (around a reference axis 300a) with respect to the body wall. Hence, unintended rotation or forward and backward movement of the outer tube 300 fixed to the exterior tube 500 with respect to the body wall is prevented.

Namely, if the outer tube 300 rotates around the reference axis 300a (around the axis) unintentionally with respect to the body wall or moves forward and backward in the direction (axial direction) of the reference axis 300a when the operation of the treatment tool 200, or the like is performed by inserting the endoscope insertion part 102 and the treatment tool insertion part 202 through the outer tube 300 after the outer tube 300 (long tubular outer tube body 320) is inserted into the body wall, there is a problem that the position of a distal end of the endoscope insertion part 102 may fluctuate and an observation visual field may fluctuate unintentionally. The exterior tube 500 prevents such unintended fluctuation of the observation visual field.

Additionally, the exterior tube 500 is provided with an air supply connector 570 for supplying a pneumoperitoneum gas (gas for pneumoperitoneum), such as carbon dioxide gas, into a body cavity. As illustrated in FIG. 1, one end of an air supply tube 122 is connected to the air supply connector 570, and the other end of the air supply tube 122 is connected to a pneumoperitoneum device 120. Accordingly, if the pneumoperitoneum gas, such as carbon dioxide gas, is supplied from the pneumoperitoneum device 120 to the air supply tube 122, the pneumoperitoneum gas is sent from the air supply connector 570 to an air supply passage in the exterior tube 500, and is delivered from a distal end of the exterior tube 500 through the air supply passage to the outside (the inside of a body cavity). In addition, the configuration of the exterior tube 500 will be described below.

Figure 4:
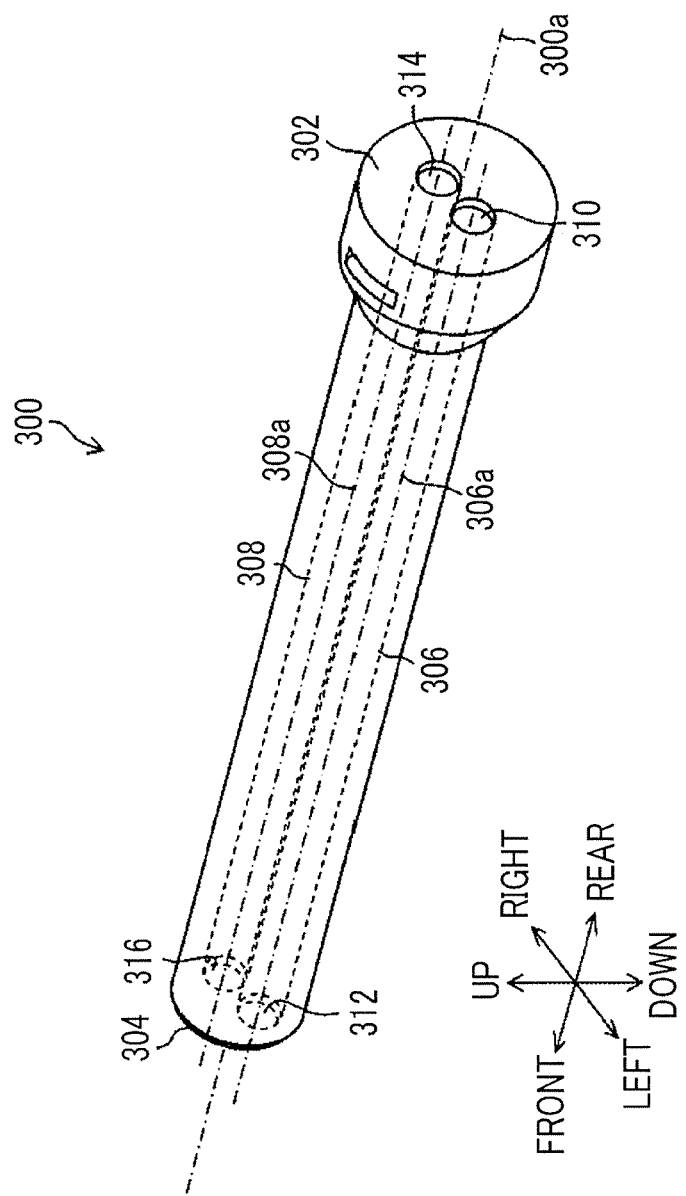
FIG. 4 is an external perspective view illustrating the outer tube.

FIG. 4 is an external perspective view illustrating the outer tube 300.

As illustrated in this drawing, the outer tube 300 has an elongated cylindrical shape as a whole, and has an endoscope insertion passage 306 through which the endoscope insertion part 102 of the endoscope 100 is inserted so as to be movable forward and backward, and a treatment tool insertion passage 308 through which the treatment tool insertion part 202 of the treatment tool 200 is inserted so as to be movable forward and backward. These insertion passages are parallel to a reference axis 300a indicating a longitudinal axis that is a central axis of the outer tube.

If a central axis of the endoscope insertion passage 306 is referred to as an endoscope insertion axis 306a and a central axis of the treatment tool insertion passage 308 is referred to as a treatment tool insertion axis 308a, the endoscope insertion axis 306a and the treatment tool insertion axis 308a are parallel to each other, and is also parallel to the reference axis 300a. The endoscope insertion axes 306a and the treatment tool insertion axes 308a are equivalent to positions of the central axis of the endoscope insertion part 102 and the central axis of the treatment tool insertion part 202 that are respectively inserted through the endoscope insertion passage 306 and the treatment tool insertion passage 308. Additionally, in the present embodiment, the reference axis 300a, the endoscope insertion axis 306a, and the treatment tool insertion axis 308a are disposed on the same plane. However, a configuration in which the reference axis 300a, the endoscope insertion axis 306a, and the treatment tool insertion axis 308a are disposed on the same plane may not be adopted.

In addition, regarding the position and orientation of a space where the outer tube 300 has been disposed, terms called forward, backward, left, right, up, and down are used with the orientation from the base end surface 302 in a direction along the reference axis 300a to the distal end surface 304 defined as the forward and with the orientation from the reference axis 300a to the endoscope insertion axis 306a defined as the left.

The base end surface 302 of the outer tube 300 is provided with a first base end opening 310 that is a base end opening that allows the endoscope insertion part 102 to be inserted into the endoscope insertion passage 306 therethrough, and a second base end opening 314 that is base end opening that allows the treatment tool insertion part 202 to be inserted into the treatment tool insertion passage 308 therethrough.

The distal end surface 304 of the outer tube 300 is provided with a first distal end opening 312 that is a distal end opening that allows the endoscope insertion part 102 inserted into the endoscope insertion passage 306 to be delivered to the outside therethrough, and a second distal end opening 316 that is a distal end opening that allows the treatment tool insertion part 202 inserted into the treatment tool insertion passage 308 to be delivered to the outside therethrough.

Figure 5:
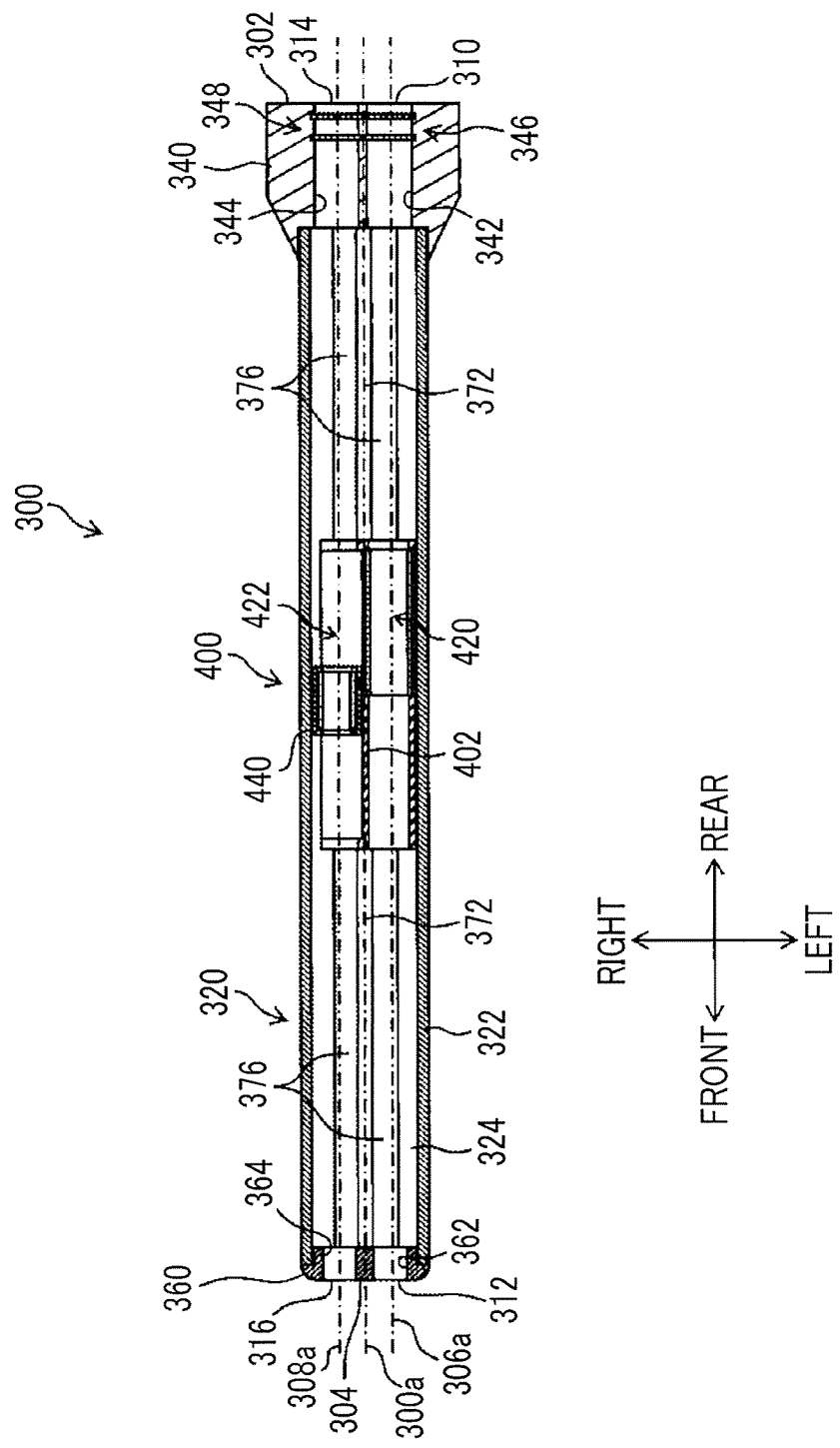
FIG. 5 is a cross sectional view illustrating the internal structure of the outer tube.

FIG. 5 is a cross sectional view illustrating the internal structure of the outer tube 300, and illustrates a cross section cut in a plane that includes the reference axis 300a and is orthogonal to an upward-downward direction (cut in a leftward-rightward direction along the reference axis 300a).

As illustrated in this drawing, the outer tube 300 has a long tubular outer tube body 320 that occupies substantially the entire area in the forward-backward direction, a base end cap 340 that is attached to a rear end (base end) of the outer tube 300, a distal end cap 360 that is attached to a distal end part, and a slider 400 that is one form of the interlocking member disposed inside the outer tube 300.

The long tubular outer tube body 320 is formed in an elongated cylindrical shape having the reference axis 300a as a central axis using hard resins, metals, or the like, and has an outer wall 322 that surrounds an outer periphery, and a cavity part 324 that penetrates from a base end of the long tubular outer tube body 320 to a distal end thereof.

The cavity part 324 includes spaces serving as the endoscope insertion passage 306 and the treatment tool insertion passage 308, and houses the slider 400 and the like.

The base end cap 340 is formed in a columnar shape of which the diameter is made larger than the external diameter of the long tubular outer tube body 320 using hard resins, metals, or the like, and a rear end surface thereof constitutes the base end surface 302 of the outer tube 300. The base end cap 340 is provided with a through-hole 342 and a through-hole 344 that form a portion of the endoscope insertion passage 306 and a portion of the treatment tool insertion passage 308, respectively. In the base end surface 302, an opening of the through-hole 342 is equivalent to the above-described first base end opening 310, and an opening of the through-hole 344 is equivalent to the above-described second base end opening 314.

Additionally, the through-holes 342 and 344 are provided with valve members 346 and 348. The valve members 346 and 348, for example, open only in a case where the endoscope insertion part 102 and the treatment tool insertion part 202 are inserted therethrough and come into close contact with outer peripheral surfaces (side surfaces) of the endoscope insertion part 102 and the treatment tool insertion part 202 without a substantial gap. This secures the airtightness of spaces closer to the distal end side than the valve members 346 and 348, and reduces the leakage or the like of a pneumoperitoneum gas injected into the body cavity to the outside of the body.

The distal end cap 360 is formed of hard resins, metals, or the like, and a distal end surface thereof constitutes the distal end surface 304 of the outer tube 300. The distal end cap 360 is provided with a through-hole 362 and a through-hole 364 that form a portion of the endoscope insertion passage 306 and a portion of the treatment tool insertion passage 308, respectively. In the distal end surface 304, an opening of the through-hole 362 is equivalent to the above-described first distal end opening 312, and an opening of the through-hole 364 is equivalent to the second distal end opening 316.

In addition, the long tubular outer tube body 320, the base end cap 340, and the distal end cap 360 show one form of constituent members that constitutes the outer tube body of the outer tube 300, and the outer tube body is not limited to the above configuration. For example, the long tubular outer tube body 320 and the base end cap 340 or the long tubular outer tube body 320 and the distal end cap 360 may be integrally formed, or may be integrally formed in their entirety.

Additionally, the outer tube body may have the following configurations.

Namely, the outer tube body has a distal end, a base end, and a longitudinal axis, and includes a first distal end opening and a second distal end opening equivalent to the above-described first distal end opening 312 and second distal end opening 316 that are provided at the distal end of the outer tube body, and a first base end opening and a second base end opening equivalent to the above-described first base end opening 310 and the second base end opening 314 that are provided at the base end of the outer tube body. The outer tube body just has to include an endoscope insertion passage and a treatment tool insertion passage equivalent to the above-described endoscope insertion passage 306 and treatment tool insertion passage 308 that are provided along the longitudinal axis of the outer tube body, that is, the endoscope insertion passage that communicates with the first distal end opening and the first base end opening and allows the endoscope 100 to be inserted therethrough so as to be movable forward and backward, and the treatment tool insertion passage that communicates with the second distal end opening and the second base end opening and allows the treatment tool 200 to be inserted therethrough so as to be movable forward and backward.

The slider 400 is housed within (the cavity part 324) the long tubular outer tube body 320, and is supported so as to be movable forward and backward in the direction of the reference axis 300a. The slider 400 is an interlocking member that is coupled to the endoscope insertion part 102 inserted through the endoscope insertion passage 306 and the treatment tool insertion part 202 inserted through the treatment tool insertion passage 308 and that has a non-sensing region where the forward and backward movement of either the endoscope insertion part or the treatment tool insertion part in the forward-backward direction (axial direction) does not interlock with the movement of the other and a sensing region where the forward and backward movement of either the endoscope insertion part or the treatment tool insertion part interlocks with the movement of the other. That is, the endoscope insertion part 102 is adapted to interlock with the forward and backward movement of the treatment tool insertion part 202 in the axial direction with play by the slider 400.

Figure 6:
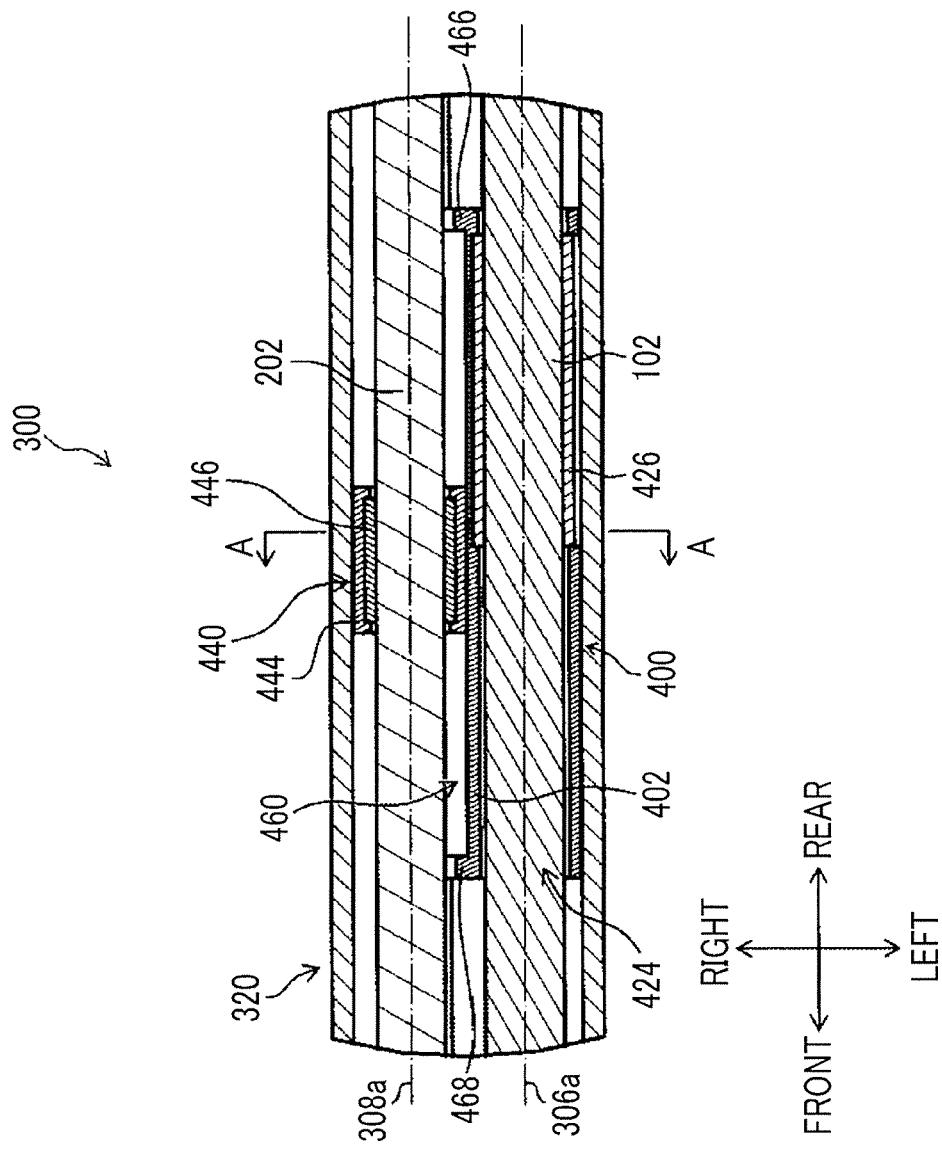
FIG. 6 is an enlarged cross sectional view illustrating a portion of FIG. 5 in an enlarged manner.
Figure 7:
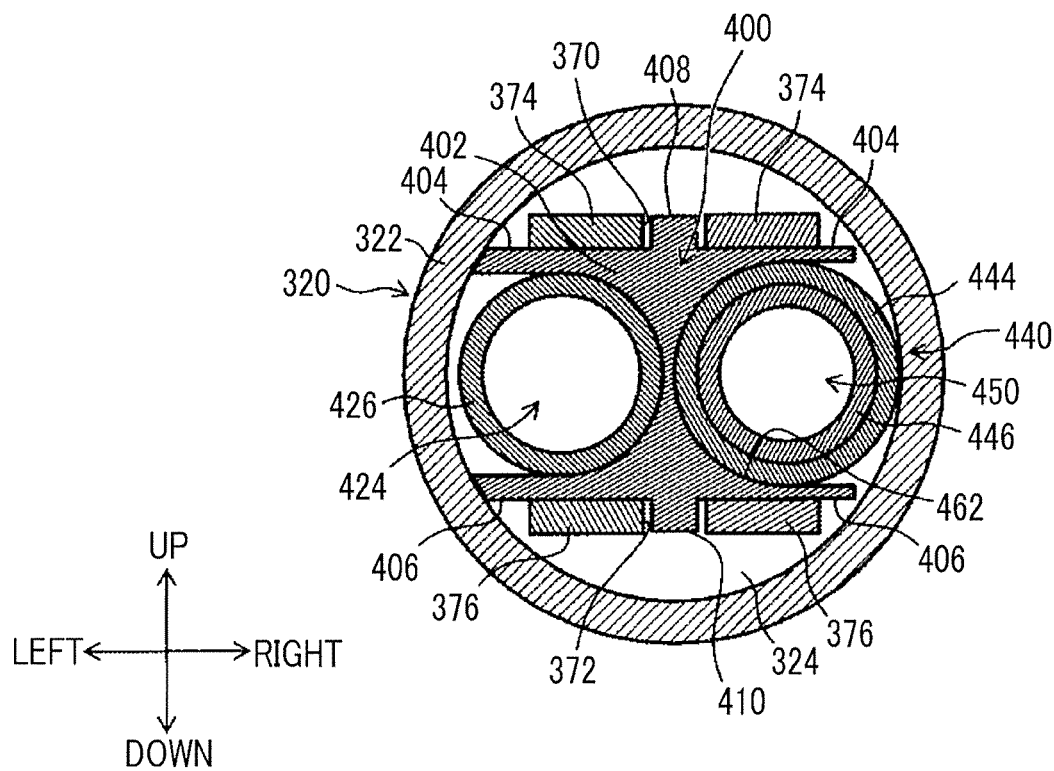
FIG. 7 is a cross sectional view as viewed from arrow A-A in FIG. 6.

FIG. 6 is an enlarged cross sectional view illustrating a portion, in which the slider 400 is disposed in FIG. 5, in an enlarged manner, and illustrates a state where the endoscope insertion part 102 and the treatment tool insertion part 202 have been inserted through the endoscope insertion passage 306 and the treatment tool insertion passage 308, respectively. FIG. 7 is a cross sectional view as seen from arrow A-A in FIG. 6.

Figure 8:
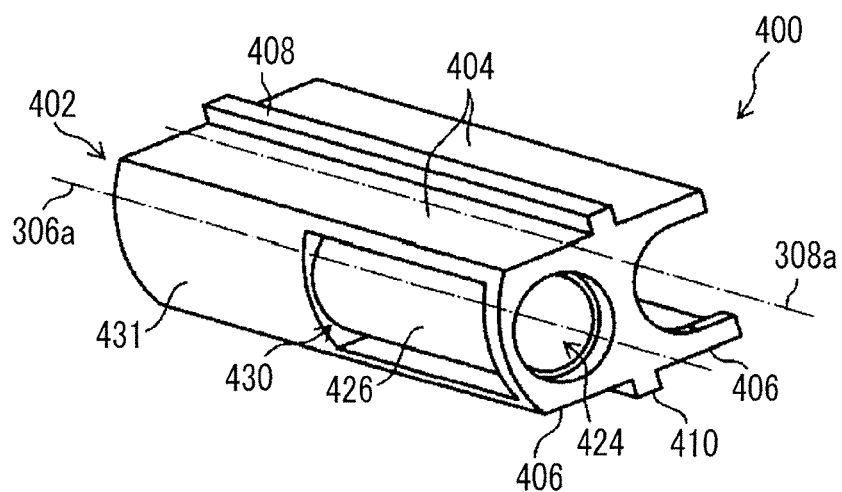
FIG. 8 is a perspective view illustrating a slider (interlocking member) from the rear upper left side.
Figure 9:
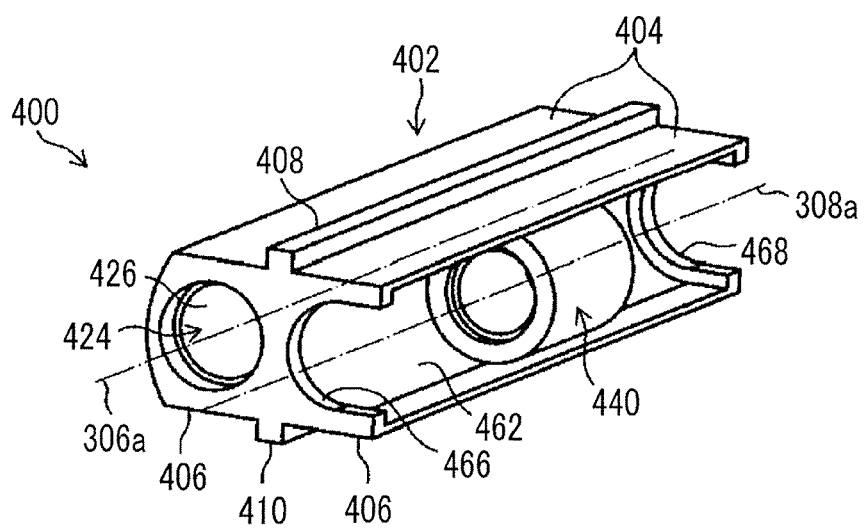
FIG. 9 is a perspective view illustrating the slider (interlocking member) from the rear upper right side.

Additionally, FIGS. 8 and 9 are respectively perspective views illustrating the slider 400 from the rear upper left and from the rear upper right.

As illustrated in these drawings, the slider 400 has a slider body 402 that holds components of the slider 400. As illustrated in FIG. 7, protruding strips 408 and 410 that extend in the direction (forward-backward direction) of the reference axis 300a are formed on a flat upper surface 404 (refer to FIGS. 8 and 9) and a flat lower surface 406 of the slider body 402.

Meanwhile, a pair of left and right long plate-shaped guide plates 374 and 374 and a pair of left and right long plate-shaped guide plates 376 and 376, which are laid between the base end cap 340 and the distal end cap 360 and illustrated in FIG. 7, are respectively supported by an upper part and a lower part within the long tubular outer tube body 320, and the guide grooves 370 and 372, which extend in the direction of the reference axis 300a from the base end cap 340 to the distal end cap 360, are formed by a gap between the guide plates 374 and 374 and a gap between the guide plates 376 and 376.

The protruding strips 408 and 410 of the slider body 402 are respectively fitted into the guide grooves 370 and 372 within the long tubular outer tube body 320, and the upper surface 404 and the lower surface 406 are disposed in a state where these surfaces have contacted or approached the guide plates 374 and 374 and the guide plates 376 and 376.

Accordingly, the slider 400 is supported so as to be movable forward and backward in the forward-backward direction within the long tubular outer tube body 320, and is supported in a state where the movement of the slider in the upward-downward direction and in the leftward-rightward direction and the rotation of the slider in all directions (directions around three axes including a forward-backward axis, a leftward-rightward axis, and an upward-downward direction) are restricted (a state where the rotation of the slider around at least the reference axis 300a is impossible). Additionally, the slider 400 moves forward and backward within a movable range having a position where the slider abuts against the base end cap 340 as a rear end, and having a position where the slider abuts against the distal end cap 360 as a front end.

In addition, the guide grooves 370 and 372 may not be formed by the guide plates 374 and 374 and the guide plates 376 and 376 disposed within the long tubular outer tube body 320, and may be formed in the outer wall 322 of the long tubular outer tube body 320 or may be formed by other configurations.

Additionally, the slider 400, as illustrated in FIG. 5, has a left endoscope-coupling part 420 that is coupled to (engaged with) the endoscope insertion part 102, and a right treatment tool-coupling part 422 that is coupled to (engaged with) the treatment tool insertion part 202.

The endoscope-coupling part 420 provided on the left side of the slider body 402 secures a space serving as the endoscope insertion passage 306, within the long tubular outer tube body 320. Additionally, the endoscope-coupling part 420, as illustrated in FIG. 6, includes a through-hole 424 (refer to FIGS. 7, 8, and 9) into which the endoscope insertion part 102 is inserted, and a pressure-contact member 426 that is fixed to the through-hole 424 and is brought into pressure contact with the outer peripheral surface (side surface) of the endoscope insertion part 102 inserted through the endoscope insertion passage 306.

The pressure-contact member 426 is formed in a cylindrical shape using elastic materials, such as elastic rubber, as illustrated in FIGS. 7 and 8. The pressure-contact member 426 is fitted into up to a position coaxial with the through-hole 424 of the slider body 402 from an opening 430 formed on a left side surface 431 of the slider body 402 and fixed to the slider body 402, as illustrated in FIG. 8.

Accordingly, when the endoscope insertion part 102 has been inserted through the endoscope insertion passage 306, as illustrated in FIG. 6, the endoscope insertion part 102 is inserted through the through-hole 424, and the pressure-contact member 426 is brought into pressure contact with (engaged with) the outer peripheral surface of the endoscope insertion part 102. Accordingly, the central axis of the endoscope insertion part 102 is disposed coaxially with the endoscope insertion axis 306a.

The endoscope insertion part 102 and the slider 400 (slider body 402) are coupled to (engaged with) each other in an interlockable manner via the pressure-contact member 426, and the slider 400 (slider body 402) also integrally moves forward and backward in an interlocking manner with the forward and backward movement of the endoscope insertion part 102 in the forward-backward direction (axial direction).

In addition, since the coupling herein is based on the elastic force of the pressure-contact member 426, the engagement position (the position of the endoscope insertion part 102 where the slider 400 is engaged) of the endoscope insertion part 102 coupled to the slider 400 (slider body 402) can be arbitrarily adjusted.

The treatment tool-coupling part 422 provided on the right side of the slider body 402 as illustrated in FIG. 5, as illustrated in FIG. 6, includes a sleeve 440 (refer to FIGS. 7 and 9) that is coupled to the treatment tool insertion part 202, and a guide part 460 that guides the sleeve 440 so as to be movable forward and backward in the forward-backward direction.

The sleeve 440, as illustrated in FIG. 7, includes a sleeve body 444 (frame body) formed in a cylindrical shape, and a pressure-contact member 446 fixed to the inside of the sleeve body 444. The pressure-contact member 446 is formed in a cylindrical shape using elastic materials, such as elastic rubber.

Accordingly, when the treatment tool insertion part 202 has been inserted through the treatment tool insertion passage 308, as illustrated in FIG. 6, the treatment tool insertion part 202 is inserted through the inside (the through-hole 450 of FIG. 7) of the pressure-contact member 446, the pressure-contact member 446 is brought into pressure contact with (engaged with) the outer peripheral surface of the treatment tool insertion part 202. Accordingly, the central axis of the treatment tool insertion part 202 is disposed coaxially with the treatment tool insertion axis 308a.

The treatment tool insertion part 202 and the sleeve 440 are coupled to each other in an interlockable manner via the pressure-contact member 446, and the sleeve 440 also integrally moves forward and backward in an interlocking manner with the forward and backward movement of the treatment tool insertion part 202 in the forward-backward direction (axial direction).

Additionally, the sleeve 440 also rotates with respect to the slider body 402 in an interlocking manner with the rotation of the treatment tool insertion part 202 around the axis thereof.

In addition, since the coupling between the treatment tool insertion part 202 and the sleeve 440 herein is based on the elastic force of the pressure-contact member 446, the engagement position (the position of the treatment tool insertion part 202 where the sleeve 440 is engaged) of the treatment tool insertion part 202 coupled to the sleeve 440 can be arbitrarily adjusted.

Meanwhile, the guide part 460 of the treatment tool-coupling part 422, as illustrated in FIGS. 7 and 9, is formed by a space surrounded by a guide surface 462 of the slider body 402 that extends in the direction of the reference axis 300a (treatment tool insertion axis 308a), within the cavity part 324 of the long tubular outer tube body 320, and an inner peripheral surface of the long tubular outer tube body 320. The sleeve 440 is housed and disposed in the space of the guide part 460, is supported so as to be movable in the forward-backward direction and rotatable around its axis, and is supported in a state where the movement of the sleeve in the upward-downward direction and in the leftward-rightward direction is restricted.

Additionally, the guide part 460 is provided so as to fall within a range from a base end of the slider body 402 to a distal end thereof, and as illustrated in FIGS. 6 and 9, has end edge parts 466 and 468, which are formed to protrude in a direction orthogonal to the guide surface 462 along an end edge of the guide surface 462, respectively, on the base end side and the distal end side of the slider body 402.

The end edge parts 466 and 468 abut against the end of the sleeve 440 to restrict the movement of the sleeve 440, when the sleeve 440 disposed in the space of the guide part 460 moves forward and backward in the forward-backward direction.

Hence, the sleeve 440 moves forward and backward within a movable range having a position where the sleeve abuts against the end edge part 466 as a rear end, and having a position where the sleeve abuts against the end edge part 468 as a front end. However, the rear end and the front end of the movable range of the sleeve 440 may not be restricted by the end edge part 466 and the end edge part 468.

The working of the slider 400 configured as described above will be described together with the operation when the treatment of a diseased site within a patient's body cavity is performed using the surgical apparatus for an endoscope 10.

Figure 13:
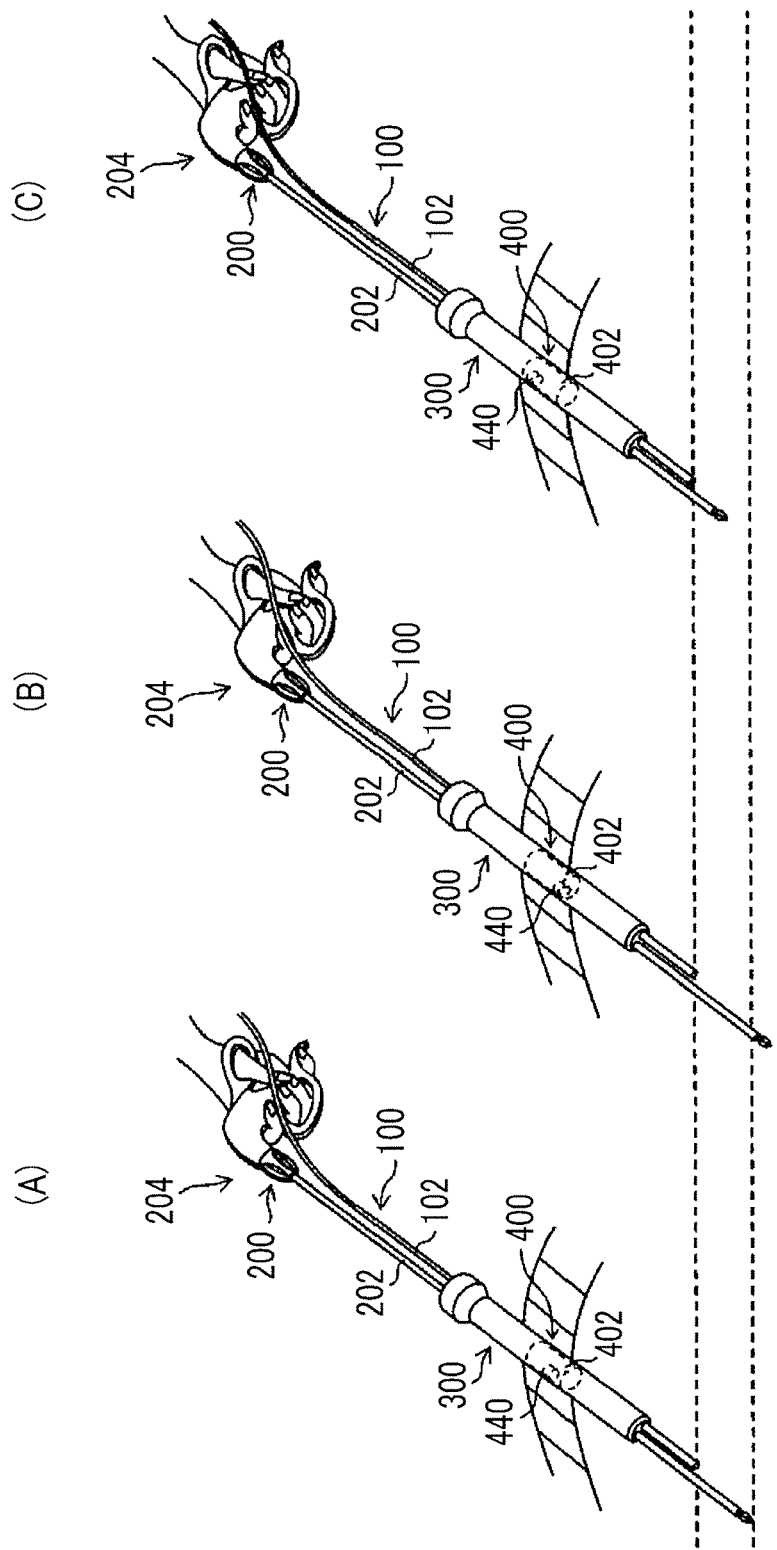
FIG. 13 is an explanatory view illustrating a state of the operation when the treatment of a diseased site within a patient's body cavity is performed using the surgical apparatus for an endoscope.
Figure 14:
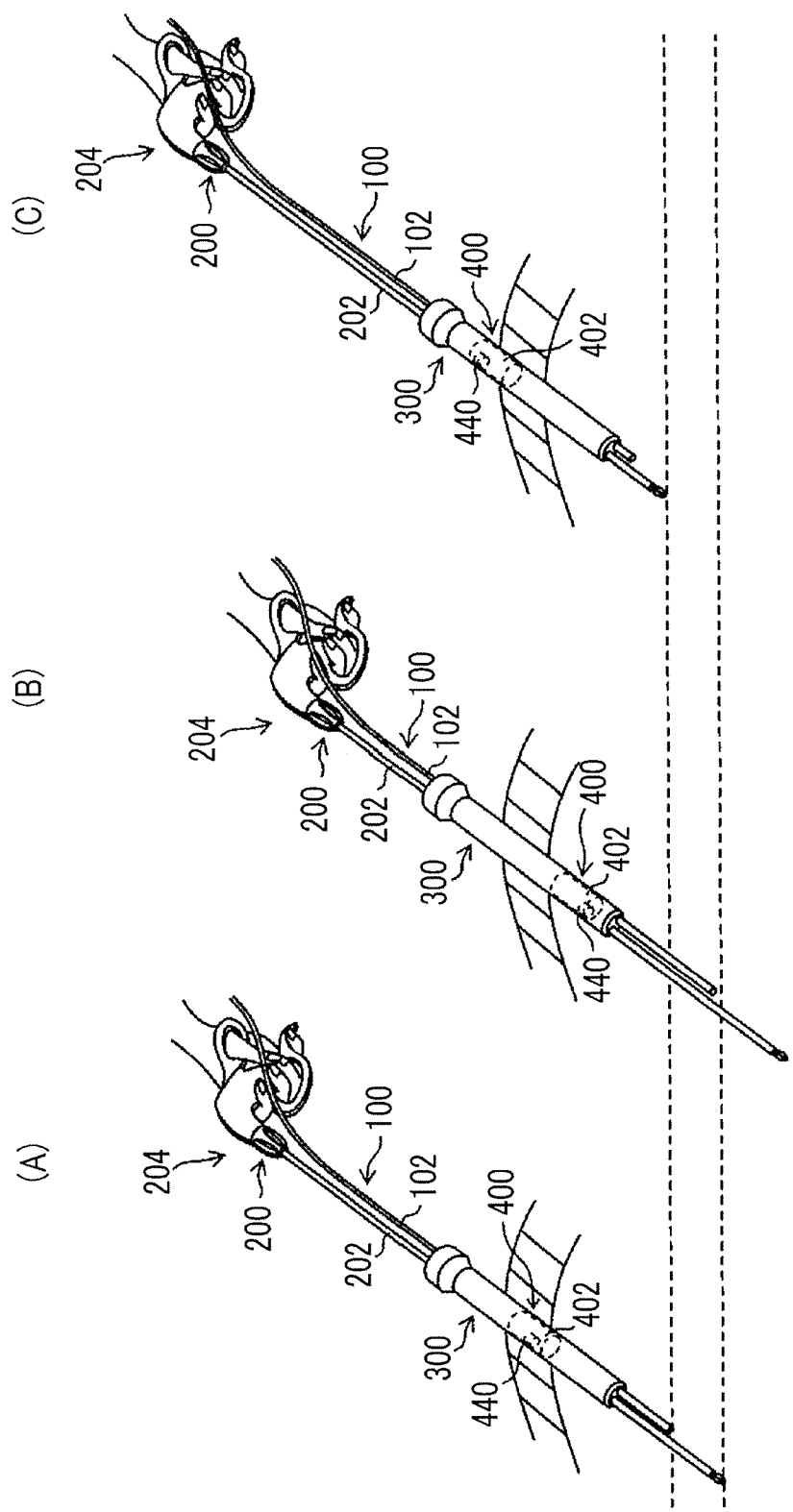
FIG. 14 is an explanatory view illustrating a state of the operation when the treatment of the diseased site within the patient's body cavity is performed using the surgical apparatus for an endoscope.

First, as illustrated in (A) part of FIG. 13, after the outer tube 300 is inserted into a patient's body wall and a pneumoperitoneum gas is injected into a body cavity, the endoscope 100 (endoscope insertion part 102) and the treatment tool 200 (treatment tool insertion part 202) are respectively inserted into the endoscope insertion passage 306 and the treatment tool insertion passage 308 of the outer tube 300, and the endoscope insertion part 102 and the treatment tool insertion part 202 are mounted on the outer tube 300. In this case, the endoscope insertion part 102 is coupled to the slider body 402 of the slider 400, and the treatment tool insertion part 202 is coupled to the sleeve 440 of the slider 400. In addition, although the exterior tube 500 is not illustrated in FIG. 13, and FIG. 14 illustrated therebelow, the exterior tube 500 is fitted to the outer tube 300 as illustrated in FIG. 3. Additionally, the forward and backward movement operating part 130 of the endoscope 100 is also omitted in the drawings.

Figure 10:
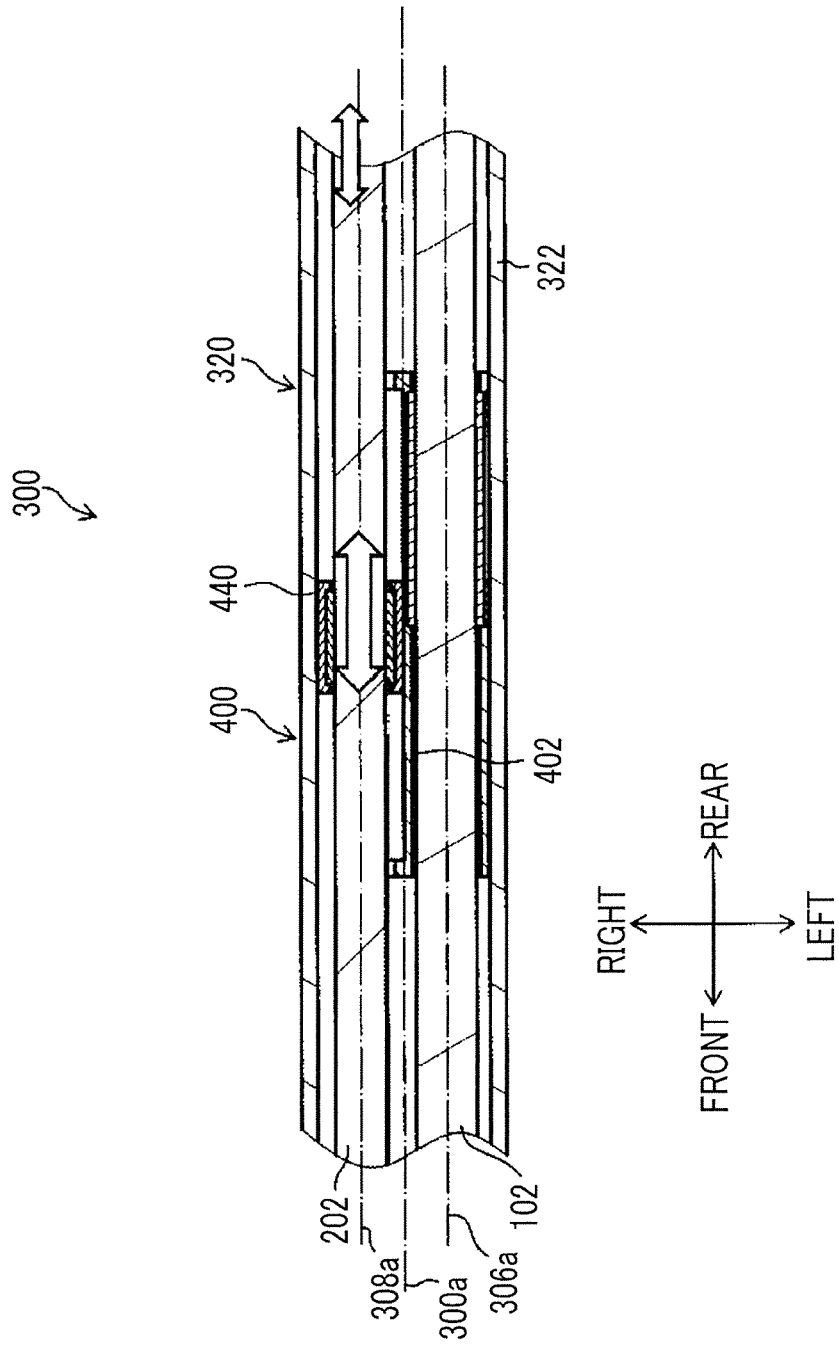
FIG. 10 is an explanatory view used for the description of the working of the slider (interlocking member).

Supposing the state of (A) part of FIG. 13 is a state where the sleeve 440 reaches neither the front end nor the rear end of the movable range thereof with respect to the slider body 402 (guide part 460) as illustrated in FIG. 10, and if an operator minutely moves the treatment tool insertion part 202 forward with his/her hand that is gripping the operating part 204 of the treatment tool 200, the slider body 402 does not move with respect to the outer tube 300 (long tubular outer tube body 320), but only the sleeve 440 moves forward with respect to the slider body 402 within the movable range thereof with respect to the slider body 402. For that reason, with respect to the forward movement of the treatment tool insertion part 202 until the sleeve 440 reaches the front end of the movable range thereof with respect to the slider body 402, as illustrated in (B) part of FIG. 13, only the treatment tool insertion part 202 moves forward in a state where the endoscope insertion part 102 is stationary. That is, the slider 400 has the non-sensing region where the endoscope insertion part 102 does not interlock with the forward and backward movement of the treatment tool insertion part 202, and the forward movement operation of the treatment tool 200 at this time becomes a forward and backward movement operation of the slider 400 in the non-sensing region.

Similarly, supposing the state of (A) part of FIG. 13 is a state where the sleeve 440 reaches neither the front end nor the rear end of the movable range thereof with respect to of the slider body 402 (guide part 460) as illustrated in FIG. 10, and if the operator minutely moves the treatment tool insertion part 202 backward with his/her hand that is gripping the operating part 204 of the treatment tool 200, the slider body 402 does not move with respect to the outer tube 300 (long tubular outer tube body 320), but only the sleeve 440 moves backward with respect to the slider body 402 within the movable range thereof with respect to the slider body 402. For that reason, with respect to the backward movement of the treatment tool insertion part 202 until the sleeve 440 reaches the rear end of the movable range thereof with respect to the slider body 402, as illustrated in (C) part of FIG. 13, only the treatment tool insertion part 202 moves backward in a state where the endoscope insertion part 102 is stationary. That is, the backward movement operation of the treatment tool 200 at this time becomes a backward movement operation of the slider 400 in the non-sensing region.

Hence, since the endoscope 100 does not move forward and backward with respect to the minute forward and backward movement operation of the treatment tool 200, that is, the forward and backward movement operation thereof in the non-sensing region, the range of an observation image to be displayed on the monitor 112 does not vary, and the size of a target to be observed can be prevented from fluctuating according to minute displacement of the treatment tool 200. Accordingly, a sense of perspective can be suitably maintained, and a stable observation image can be provided.

Figure 11:
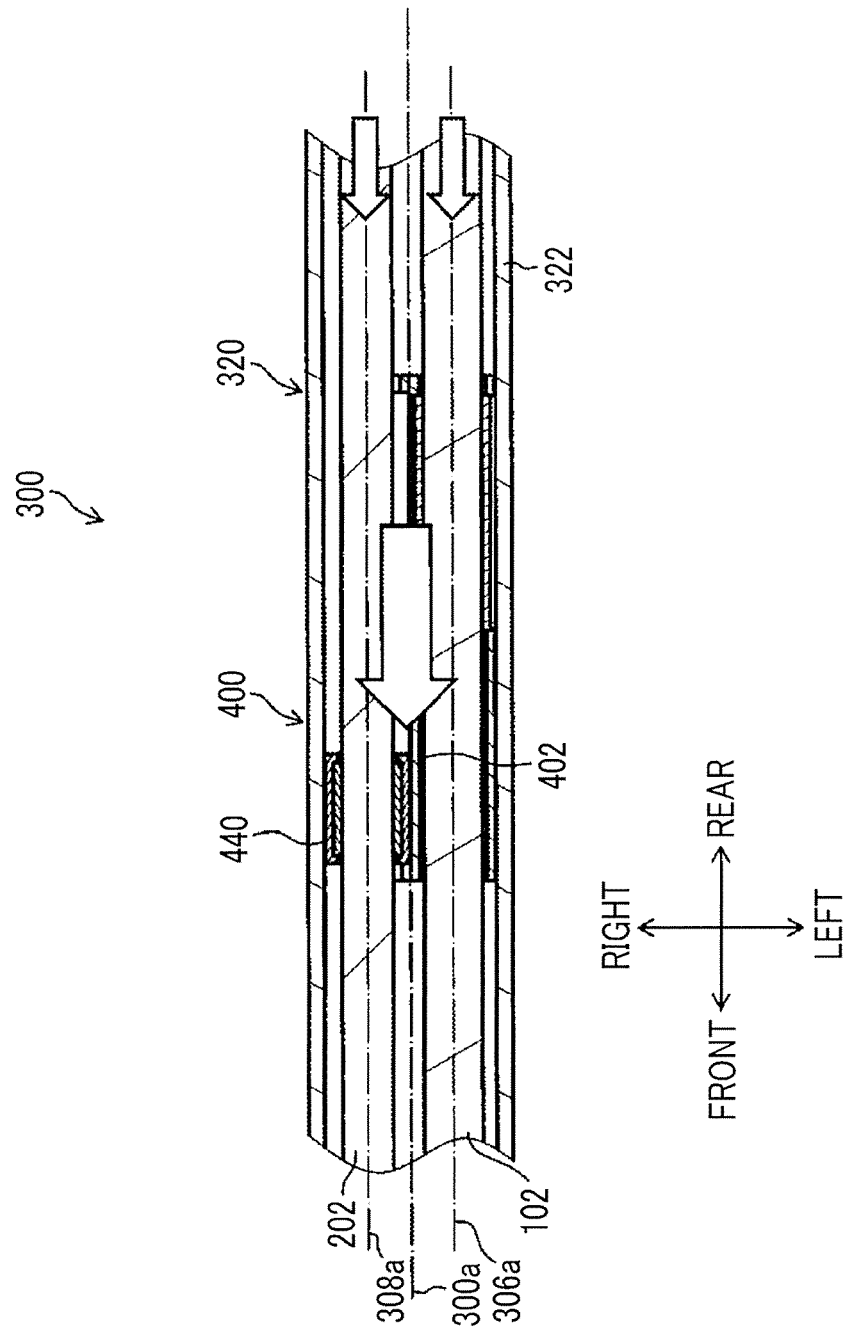
FIG. 11 is an explanatory view used for the description of the working of the slider (interlocking member).

Meanwhile, if the operator greatly moves the treatment tool insertion part 202 forward with his/her hand that is gripping the operating part 204 of the treatment tool 200 in a state where the sleeve 440 reaches neither the front end nor the rear end of the movable range thereof with respect the slider body 402 as illustrated in FIG. 10, a state where the sleeve 440 reaches the front end of the movable range thereof with respect to the slider body 402 as illustrated in FIG. 11 is brought into after the forward movement of the sleeve 440 of the slider 400 in the non-sensing region until it abuts against the front end of the movable range. Then, if the treatment tool insertion part 202 further moves forward, the sleeve 440 and the slider body 402 moves forward with respect to the long tubular outer tube body 320 together with the treatment tool insertion part 202. As a result, the endoscope insertion part 102 moves forward in an interlocking manner with the treatment tool insertion part 202. For that reason, with respect to the forward movement of the treatment tool insertion part 202 after the sleeve 440 reaches the front end of the movable range thereof with respect to the slider body 402, the endoscope insertion part 102 moves forward in an interlocking manner with the treatment tool insertion part 202 as illustrated in (B) part of FIG. 14, compared to the state of (A) part of FIG. 14 illustrating the same state as (A) part of FIG. 13. That is, the slider 400 has the sensing region where the endoscope insertion part 102 interlocks with the forward and backward movement of the treatment tool insertion part 202, and the forward movement operation of the treatment tool 200 at this time becomes a forward movement operation of the slider 400 in the sensing region.

Figure 12:
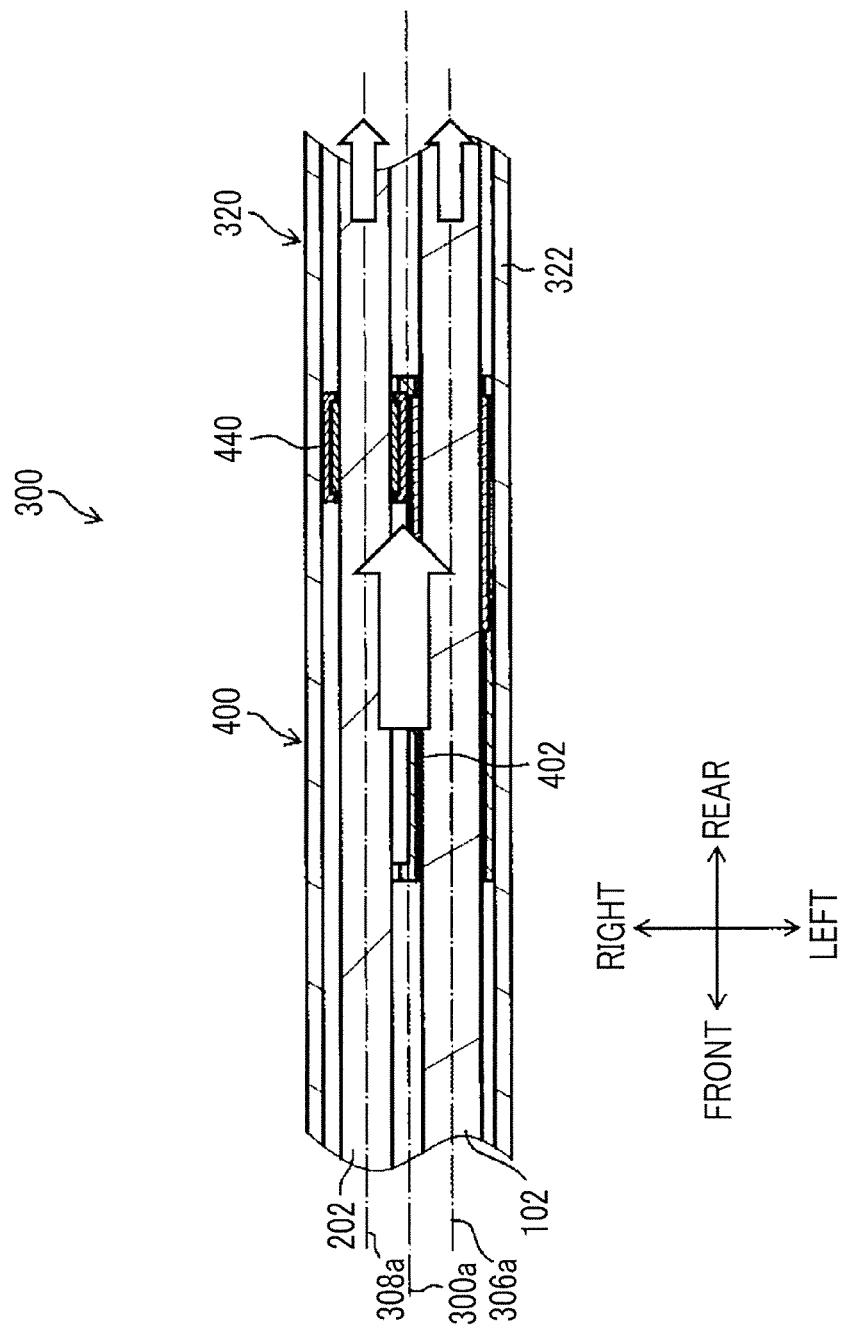
FIG. 12 is an explanatory view used for the description of the working of the slider (interlocking member).

Similarly, if the operator greatly moves the treatment tool insertion part 202 backward with his/her hand that is gripping the operating part 204 of the treatment tool 200 in a state where the sleeve 440 reaches neither the front end nor the rear end of the movable range thereof with respect the slider body 402 as illustrated in FIG. 10, a state where the sleeve 440 reaches the rear end of the movable range thereof with respect to the slider body 402 as illustrated in FIG. 12 is brought into after the backward movement of the sleeve 440 of the slider 400 in the non-sensing region until it abuts against the rear end of the movable range. Then, if the treatment tool insertion part 202 further moves backward, the sleeve 440 and the slider body 402 moves backward with respect to the long tubular outer tube body 320 together with the treatment tool insertion part 202. As a result, the endoscope insertion part 102 moves backward in an interlocking manner with the treatment tool insertion part 202. For that reason, with respect to the backward movement of the treatment tool insertion part 202 after the sleeve 440 reaches the rear end of the movable range thereof with respect to the slider body 402, as illustrated in (C) part of FIG. 14, the endoscope insertion part 102 moves backward in an interlocking manner with the treatment tool insertion part 202. That is, the backward movement operation of the treatment tool 200 at this time becomes a backward movement operation of the slider 400 in the sensing region.

Hence, since the endoscope 100 moves forward and backward with respect to a large forward and backward movement operation of the treatment tool 200, that is, the forward and backward movement operation thereof in the sensing region, the range of an observation image to be displayed on the monitor 112 is continuously changed so as to follow the forward and backward movement of the treatment tool 200. Accordingly, since the size of a target to be observed varies according to the operation of the treatment tool 200, the operator can simply obtain a desired image.

As described above, in a case where the displacement of the treatment tool insertion part 202 in the axial direction is large (in a case where a large amplitude of forward and backward movement has been performed) when an operator has moved the treatment tool insertion part 202 forward and backward in the axial direction, the endoscope insertion part 102 also moves in an interlocking manner forward, backward, up, down, right, and left. Thus, the visual field, orientation, and the like of the endoscope 100 can be changed as intended by an operator. Additionally, the visual field is always given to pick up an image of the distal end of the treatment tool, and consequently, an image that is optimal for treatment is automatically provided. In a case where it is desired to check sites other than a site to be treated, the checking can be performed by moving the treatment tool insertion part 202, and an operator can perform operations as desired. Hence, an assistant (endoscopic technician) who operates the endoscope 100 apart from the operator can be made unnecessary, and a troublesome condition in which the operator should instruct an assistant about the visual field, orientation, and the like of the endoscope 100 serially can be eliminated.

Additionally, in a case where the displacement of the treatment tool insertion part 202 in the axial direction is small (in a case where a small amplitude of forward and backward movement has been performed), the endoscope insertion part 102 does not interlock. Therefore, the size of a target to be observed within an observation image can be prevented from fluctuating unnecessarily, a sense of perspective can be suitably maintained, and a stable observation image can be provided.

Next, the exterior tube 500 illustrated in FIGS. 1 and 3 will be described.

Figure 15:
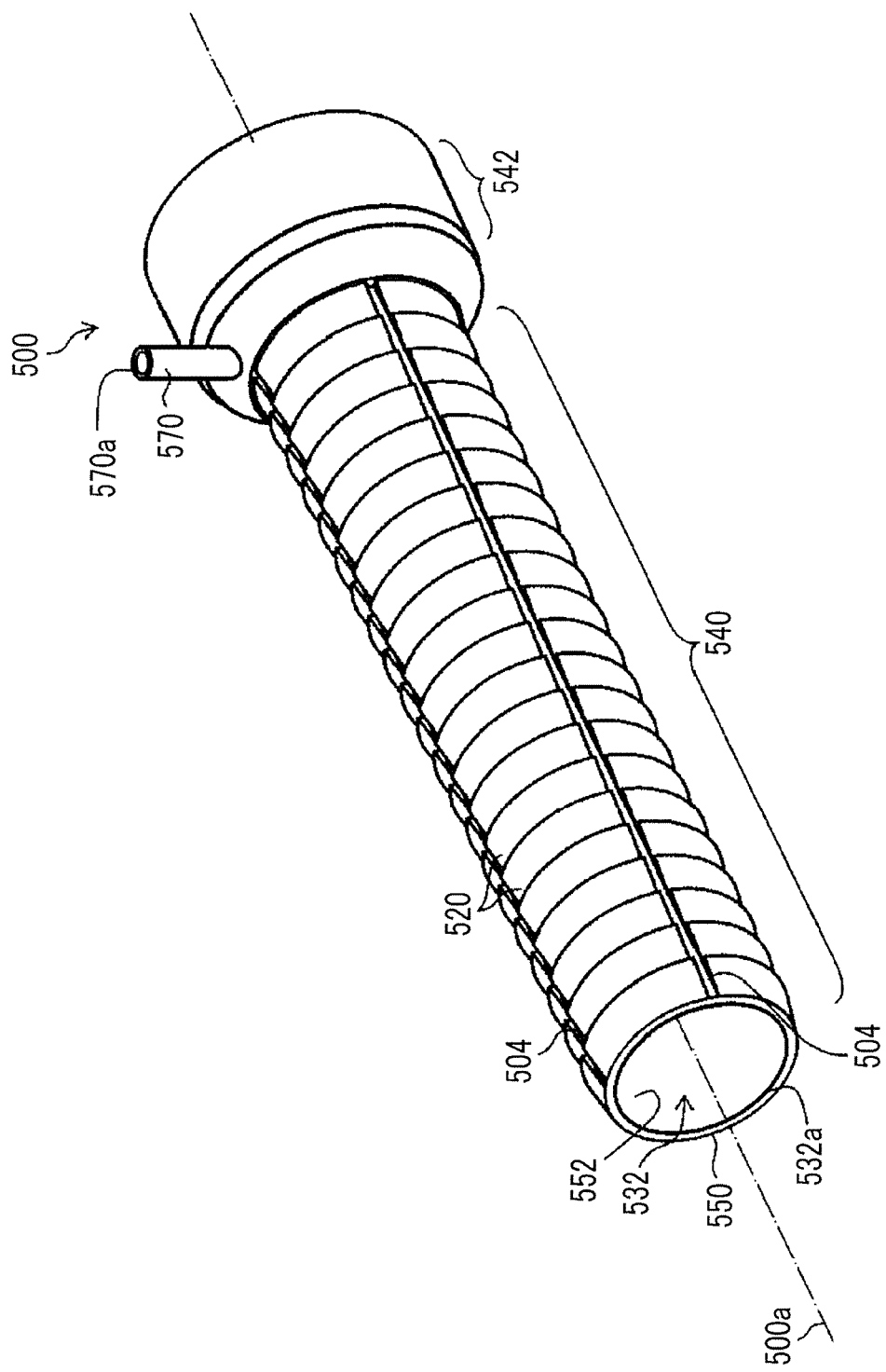
FIG. 15 is a perspective view of the exterior tube.

FIG. 15 is a perspective view illustrating only the exterior tube 500.

As illustrated in FIGS. 3 and 15, the exterior tube 500 is formed in a long tubular shape having a reference axis 500a as a longitudinal axis (central axis), and has an insertion passage 532 passing therethrough along the reference axis 500a (axial direction) from a base end of the exterior tube 500 to a distal end thereof.

The insertion passage 532 is a through-hole through which the outer tube 300 is inserted, and has a diameter of a size such that the long tubular outer tube body 320 of the outer tube 300 is movable forward and backward in the axial direction and is inserted therethrough so as to be rotatable in a direction around its axis.

In addition, in the following, a range including a portion closer to the distal end side than a distal end of the base end cap 340 of the outer tube 300, that is, a portion exposed to the outside of the long tubular outer tube body 320, and the distal end cap 360 is referred to as an outer tube insertion part 321.

If the outer tube insertion part 321 is inserted into the insertion passage 532 from the base end side and moved forward and backward, the outer tube insertion part 321 is delivered from a distal end side of the insertion passage 532. Accordingly, as illustrated in FIG. 3, the exterior tube 500 is fitted to an outer peripheral surface of the outer tube insertion part 321, and is sheathed to the exterior tube 500 at a desired position of the outer tube insertion part 321 by pressure contact of the pressure-contact member to be described below.

In addition, the axial length of the exterior tube 500 is shorter than the axial length of the outer tube insertion part 321, and falls within an axial range of the outer tube insertion part 321.

The exterior tube 500 is constituted with an exterior tube insertion part 540 on a distal end side thereof, and a base end part 542 connected to a base end side of the exterior tube insertion part 540 from a base end thereof.

The exterior tube insertion part 540 is a portion that is inserted into a body wall together with the outer tube insertion part 321 inserted through the insertion passage 532 and is insertable into a hole (port) of the body wall and a body cavity, and has a distal end opening 532a (refer to FIG. 15) from which the outer tube insertion part 321 inserted through the insertion passage 532 is delivered, on a distal end side thereof.

The exterior tube insertion part 540 has an outer wall 550 in a long tubular shape that has the reference axis 500a a central axis. An inner tube 552 in a long tubular shape extending in a direction of the reference axis 500a a range from a distal end of the exterior tube insertion part 540 to the base end part 542 is disposed inside the outer wall 550, and is fixed in a state where the outer wall 550 is brought into close contact with an outer peripheral surface of the inner tube 552. Accordingly, an outer peripheral wall of the exterior tube insertion part 540 is formed of the outer wall 550 and the inner tube 552.

A cavity inside the inner tube 552 constitutes a portion of the above-described insertion passage 532 through which the outer tube insertion part 321 is inserted, and has almost the same diameter as the external diameter of the outer tube insertion part 321 (long tubular outer tube body 320).

Hence, in a state where the outer tube insertion part 321 is inserted through the insertion passage 532 of the exterior tube 500 as illustrated in FIG. 3, an inner peripheral surface of the inner tube 552 of the exterior tube 500 is disposed in contact with or close to the outer peripheral surface of the outer tube insertion part 321, and the outer wall 550 of the exterior tube insertion part 540 of the exterior tube 500 is disposed at a vicinity position along the outer peripheral surface of the outer tube insertion part 321. Additionally, the reference axis 500a of the exterior tube 500 in this case is disposed substantially coaxially with the reference axis 300a of the outer tube 300.

A locking part consisting of recesses or protrusions that restrict (lock) unintended fluctuation of the exterior tube 500 with respect to a body wall is formed in an outer peripheral surface of the outer wall 550. As one specific form of the locking part of the outer peripheral part, the four longitudinal grooves 504 that restrict the rotation of the exterior tube 500 in the direction around the axis with respect to a body wall as described above, and a number of the lateral grooves 520 that restrict the forward and backward movement of the exterior tube 500 in the axial direction with respect to the body wall are formed.

The respective longitudinal grooves 504 are linearly formed in the direction of the reference axis 500a, and the four longitudinal grooves 504 are formed at 90° intervals in the direction around the axis (a rotational direction about the reference axis 500a).

According to the longitudinal grooves 504, cells of a body wall enters the respective longitudinal grooves 504 when the outer tube 300 to which the exterior tube 500 is fitted is inserted into the body wall. Therefore, resistance occurs in the rotation of the outer tube 300 around the axis, and the unintended rotation of the outer tube 300 around the axis is prevented.

In addition, although the number of the longitudinal grooves 504 has been described as four in the present embodiment, the number may be except four.

The respective lateral grooves 520 are annularly formed in the direction around the axis, and a number of the lateral grooves 520 are periodically formed in the direction of the reference axis 500a.

Figure 16:
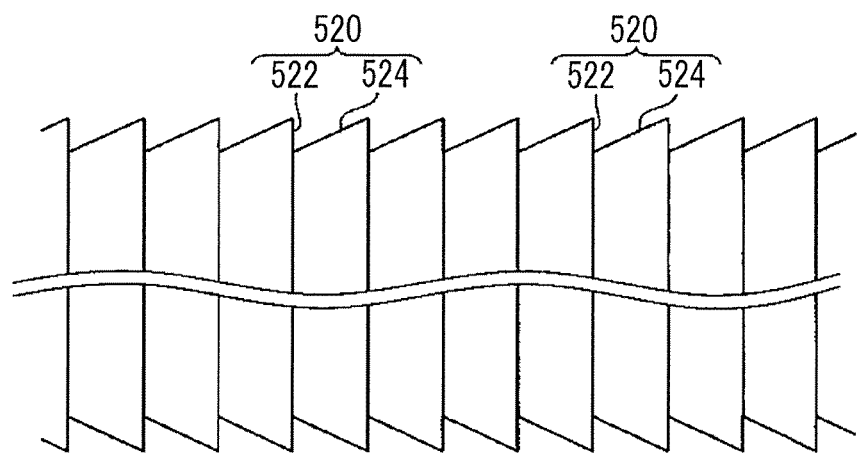
FIG. 16 is an enlarged view of an outer wall of the exterior tube.

Each lateral groove 520 is formed from a side surface 522 on the distal end side and a tapered surface 524 on the base end side as illustrated in FIG. 16 in which a portion of the outer wall 550 is enlarged, the side surface 522 restricts movement of the exterior tube 500 (outer tube 300) to the base end side in the axial direction with respect to a body wall, and the tapered surface 524 restricts movement of the exterior tube 500 (outer tube 300) to the distal end side in the axial direction with respect to the body wall.

An inclination angle (an inclination angle with respect to a radial direction perpendicular to the reference axis 500a) of the side surface 522 is smaller than an inclination angle (an inclination angle with respect to the radial direction perpendicular to the reference axis 500a) of the tapered surface 524. For example, the side surface 522 is formed parallel to the radial direction perpendicular to the reference axis 500a. In other words, a normal direction of the side surface 522 is made parallel to the reference axis 500a.

In addition, the inclination angle of the side surface 522 is not limited to this, and may be, for example, in a range of 0 degree or more and 30 degrees or less, preferably, 0 degree or more and 15 degrees or less to the distal end side or the base end side.

Meanwhile, the inclination angle of the tapered surface 524 may be larger than the inclination angle of the side surface 522, for example, may be a range of 45 degrees or more and less than 90 degrees, preferably, 60 degrees or more and less than 90 degrees to the base end side with respect to the radial direction perpendicular to the reference axis 500a.

According to the lateral grooves 520, cells of a body wall enters the respective lateral grooves 520 when the outer tube 300 to which the exterior tube 500 is fitted is inserted into the body wall. Therefore, resistance occurs in the forward and backward movement of the outer tube 300 in the axial direction, and the unintended forward and backward movement of the outer tube 300 in the axial direction is prevented.

Figure 17:
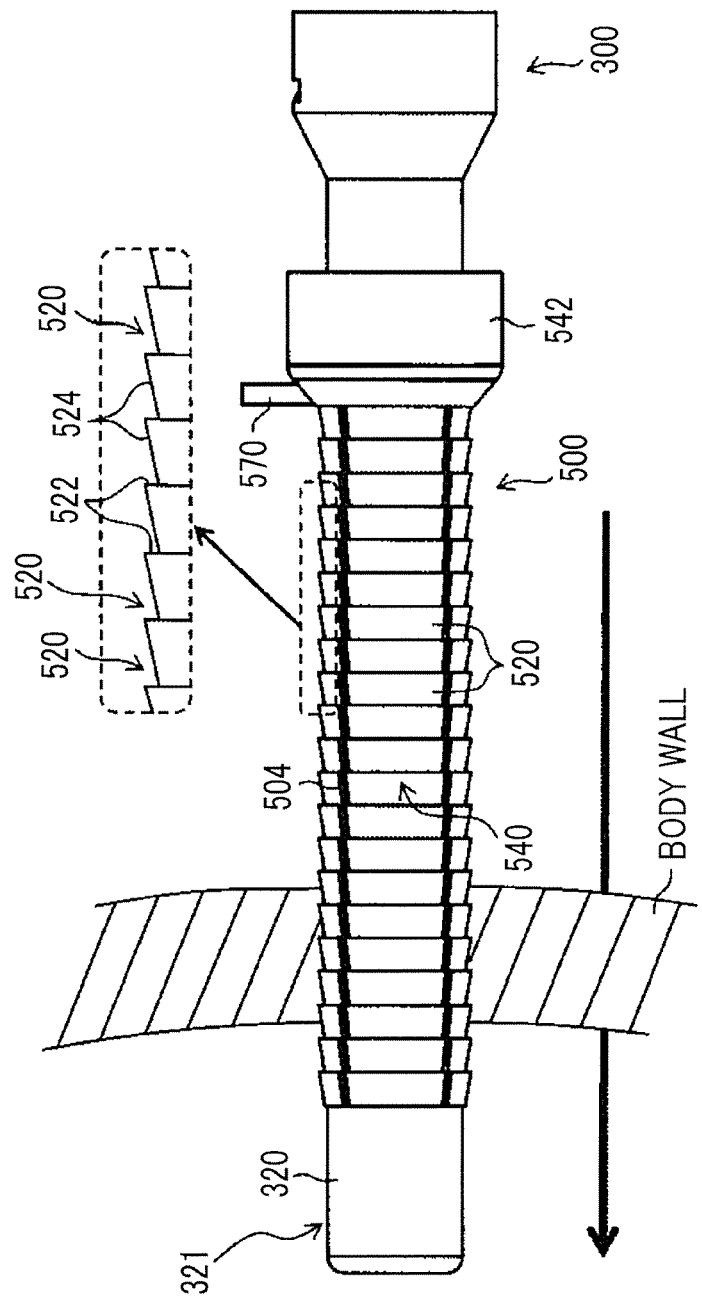
FIG. 17 is a view illustrating a state when the exterior tube is fitted to a body wall of the outer tube.

Additionally, as an aspect when the outer tube 300, to which the exterior tube 500 is fitted, is inserted into a body wall, the movement of the exterior tube is restricted by the tapered surface 524 of each lateral groove 520 when the outer tube 300 is moved forward and backward (moved forward) to the distal end side in the axial direction with respect to the body wall as illustrated in FIG. 17. In this case, since the inclination angle of the tapered surface 524 is large as described above, a large resistance force is not received as compared to a case where the outer tube 300 is moved forward and backward (moved backward) toward the base end side in the axial direction. Hence, when the outer tube 300 to which the exterior tube 500 is fitted is inserted into a body wall, a problem that it may become difficult to perform an insertion operation due to the exterior tube 500 does not occur, and a problem that the lateral grooves 520 may crush the tissue of the body wall does not occur, too.

In addition, the form of the above-described irregularities formed in an outer peripheral surface of the exterior tube insertion part 540 (outer wall 550) of the exterior tube 500 may be an example, and may be other forms.

The base end part 542 of the exterior tube 500, as illustrated in FIGS. 3 and 15, has a larger external diameter than the exterior tube insertion part 540. Accordingly, the base end part 542 is not inserted into a hole of a body wall into which the exterior tube insertion part 540 is inserted, and is disposed outside the body. Hence, even if the restriction of the forward movement of the outer tube 300, to which the exterior tube 500 is fitted, with respect to a body wall as described above is weak as compared to the backward movement of the outer tube, it is possible to adjust the position of the exterior tube 500 fixed to the outer tube 300 (outer tube insertion part 321) to use the base end part 542 at a position where the base end is made to abut against the body wall, thereby reliably preventing unintended movement of the outer tube 300 to the distal end side in the axial direction with respect to the body wall.

Figure 18:
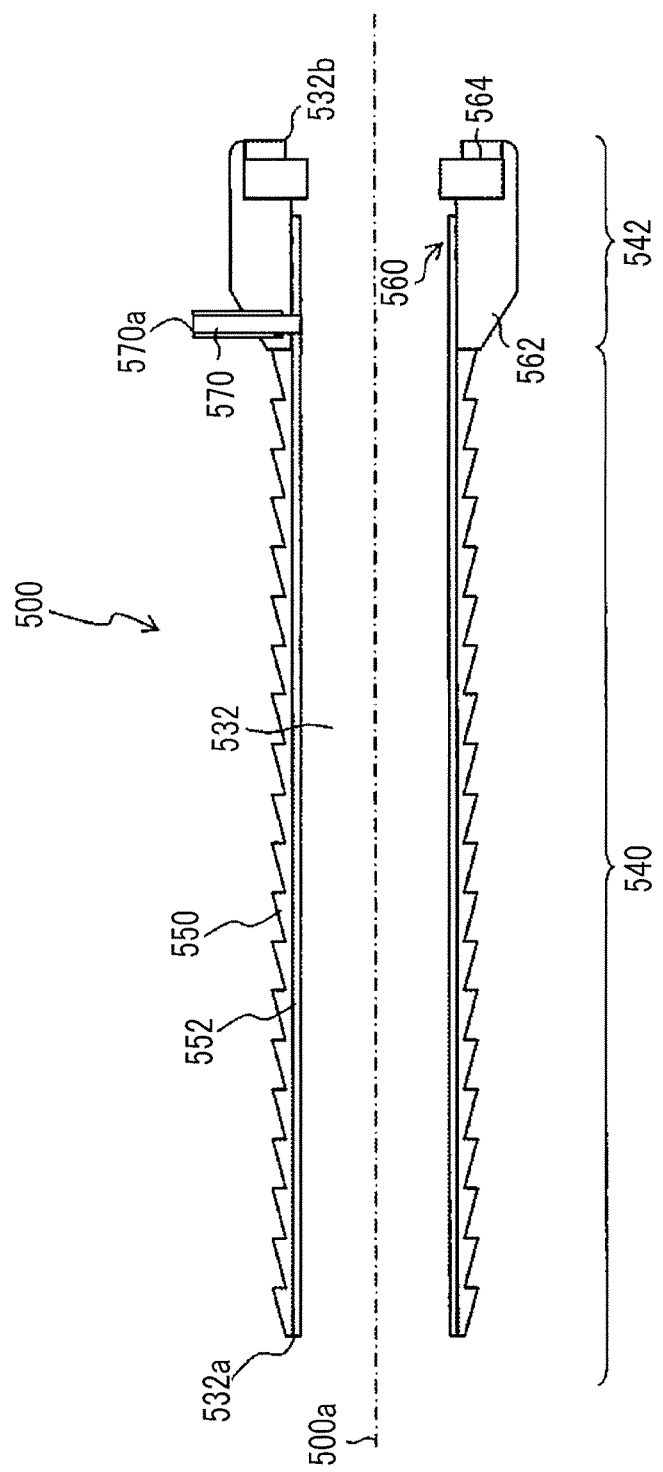
FIG. 18 is a cross sectional view when the exterior tube is cut along a reference axis.

Additionally, as illustrated in a cross sectional view along the reference axis 500a of the exterior tube 500 of FIG. 18, the base end part 542 is formed in a cylindrical shape, and has a through-hole 560 through which the outer tube insertion part 321 is inserted. The inner tube 552 extending from the distal end of the exterior tube insertion part 540 to the base end part 542 is fitted into the through-hole 560, and the base end part 542 is fixed to the inner tube 552.

In addition, the through-hole 560 forms a portion of the insertion passage 532 of the exterior tube 500 through which the outer tube insertion part 321 is inserted, and an opening of the through-hole 560 on the base end side forms a base end opening 532b of the insertion passage 532 of the exterior tube 500 through which the outer tube insertion part 321 is inserted.

A tubular airtight holding member 564 is provided in the vicinity of base end opening 532b of the through-hole 560 of the base end part 542.

The airtight holding member 564 is formed of elastic materials, such as elastic rubber, and the internal diameter thereof is slightly smaller than the external diameter of the outer tube insertion part 321 (long tubular outer tube body 320). Hence, when the exterior tube 500 is fitted into the outer tube insertion part 321, the airtight holding member 564 is brought into pressure contact with the outer peripheral surface of the outer tube insertion part 321. Accordingly, the exterior tube 500 is fixed to the outer tube insertion part 321. That is, the rotation or forward and backward movement of the outer tube 300 with respect to the exterior tube 500 is restricted by the airtight holding member 564.

Additionally, a gap between the exterior tube 500 and the outer tube insertion part 321 is covered at the position of the airtight holding member 564, and the airtightness of a space closer to the distal end side than the airtight holding member 564 is maintained. Accordingly, leakage of a pneumoperitoneum gas injected into a body cavity to the outside of the body is reduced.

However, since the fixation herein is based on the elastic force of the airtight holding member 564, the position where the exterior tube 500 is fixed to the outer tube insertion part 321 can be arbitrarily adjusted. Additionally, the exterior tube 500 can also be relatively rotated in the direction around the reference axis 300a (reference axis 500a) with respect to the outer tube insertion part 321.

Moreover, the exterior tube 500 of the present embodiment including an air supply mechanism for a pneumoperitoneum gas, and an tubular air supply connector 570 to which one end of the air supply tube 122 connected to the pneumoperitoneum device 120 as illustrated in FIG. 1 is connected is provided on an outer peripheral surface of the base end part 542 so as to protrude radially outward. In the present embodiment, although the air supply connector 570 is provided within a range of a tapered surface of the base end part 542 on the distal end side, the air supply connector may also be provided at other positions.

Figure 19:
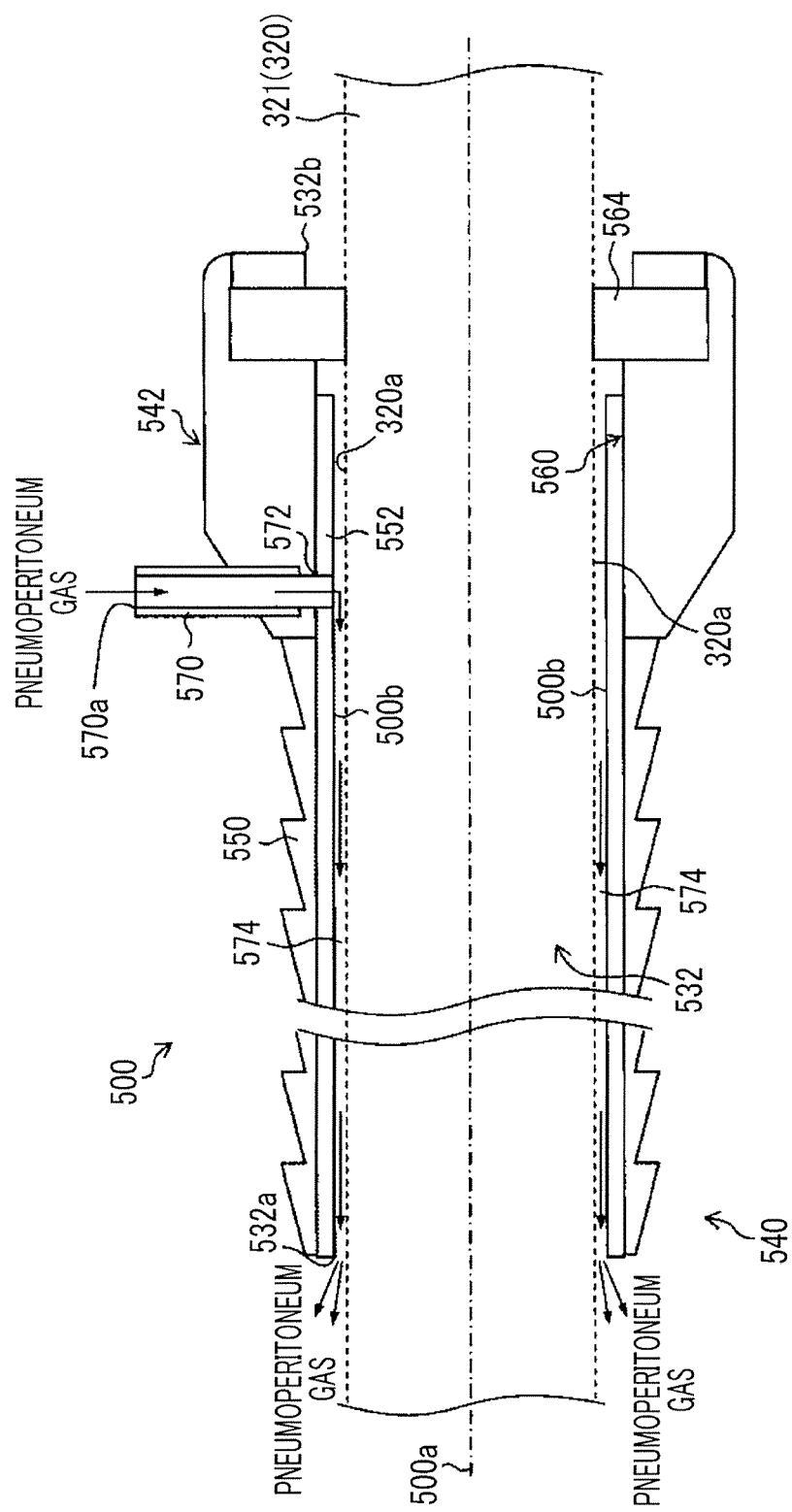
FIG. 19 is a cross sectional view illustrating a base end part and a distal end part in FIG. 18 in an enlarged manner.

As illustrated in FIG. 19 in which the base end part 542 and the distal end part of the exterior tube 500 in FIG. 18 are enlarged, the air supply connector 570 has a supply port 570a serving as an opening, and is connected to an air supply passage 572 that is formed in communication with the base end part 542 (tapered part 562) and the inner tube 552. The air supply connector 570 communicates with a cavity inside the inner tube 552 via the air supply passage 572, that is, the insertion passage 532 of the exterior tube 500, at a position closer to the distal end side than the airtight holding member 564.

Meanwhile, as illustrated by a dashed line in this drawing, in a state where the outer tube insertion part 321 (long tubular outer tube body 320) of the outer tube 300 is inserted through the insertion passage 532 of the exterior tube 500 and the exterior tube 500 is fitted to the outer tube insertion part 321, a gap is formed between an outer peripheral surface 320a of the outer tube insertion part 321 and an inner peripheral surface (that is, an inner peripheral surface 500b of the exterior tube 500) of the inner tube 552. In addition, in this drawing, a proportion that the gap occupies with respect to the other members is enlarged for description, and is different from an actual one.

The gap forms an air supply passage 574 that allows the communication from the position of the airtight holding member 564 to the distal end (distal end opening 532a) of the exterior tube 500.

Hence, the supply port 570a of the air supply connector 570 allows communication up to the distal end opening 532a of the exterior tube 500 serving as an air supply port through the air supply passage 572 of the base end part 542 and the air supply passage 574 formed by the gap.

Subsequently, the working of the air supply mechanism for a pneumoperitoneum gas in the exterior tube 500 will be described. The outer tube 300 to which the exterior tube 500 is sheathed is inserted to a body wall as illustrated in FIG. 17, and the pneumoperitoneum device 120 is connected to the air supply connector 570 via the air supply tube 122 as illustrated in FIG. 1. In this case, if a pneumoperitoneum gas is supplied to the air supply connector 570 via the air supply tube 122 from the pneumoperitoneum device 120, as illustrated in FIG. 19, the pneumoperitoneum gas is sent to the air supply passage 574 formed by the gap between the outer peripheral surface 320a of the outer tube insertion part 321 and the inner peripheral surface 500b of the exterior tube 500 through the air supply passage 572 of the base end part 542.

Since the base end side of the air supply passage 574 is covered with the airtight holding member 564, the pneumoperitoneum gas sent to the air supply passage 574 flows through the air supply passage 574 to the distal end side while widening in the circumferential direction of the inner peripheral surface 500b of the exterior tube 500 and the outer peripheral surface 320a of the outer tube insertion part 321.

The pneumoperitoneum gas that has flowed through the air supply passage 574 is delivered into a body cavity that becomes the outside of the exterior tube 500 from the distal end opening 532a (air supply port) of the distal end of the exterior tube 500.

According to the air supply mechanism for a pneumoperitoneum gas in the above exterior tube 500, the air supply tube 122 to which the pneumoperitoneum gas from the pneumoperitoneum device 120 is supplied has only to be connected to the air supply connector 570 of the exterior tube 500. Therefore, it is easy to dispose the air supply tube 122, and the endoscope 100 and the treatment tool 200 inserted through the outer tube 300 in order to avoid contact therebetween. Therefore, any twist between the air supply tube 122 and the endoscope 100 or the treatment tool 200 can be prevented in advance without paying special attention.

Additionally, by adjusting the angle (or the angle of the outer tube 300 in the direction around the axis with respect to the exterior tube 500) of the exterior tube 500 in the direction around the axis with respect to the outer tube 300, the air supply connector 570 and the air supply tube 122 can be disposed in a body wall in a direction in which the endoscope 100 and the treatment tool 200 do not interfere with each other, regardless of the angular positions of the endoscope 100 and the treatment tool 200, inserted through the outer tube 300, in the direction around the axis. Moreover, the angle of the outer tube 300 in the direction around the axis with respect to the exterior tube 500 can be set and changed to at arbitrary angles so as to bring about a state where the angular positions of the endoscope 100 and the treatment tool 200, inserted through the outer tube 300, in the direction around the axis are suitable for treatment, without the air supply tube 122 interfering with the endoscope 100 or the treatment tool 200.

Additionally, for example, compared to a case where a pneumoperitoneum gas is supplied through the endoscope insertion passage 306 and the treatment tool insertion passage 308 of the outer tube 300, regardless of the presence/absence of insertion of the endoscope 100 or the treatment tool 200 into the outer tube 300, air-supply flow rates in the air supply passages 572 and 574 can be substantially uniformly maintained, and stable supply of the pneumoperitoneum gas is possible.

Additionally, since the air supply passage 574 is formed along the outer peripheral surface 320a of the outer tube insertion part 321, the cross-sectional area of the air supply passage 574 is large, and the air-supply flow rate of the air supply passage 574 can be increased. The external diameter of the outer tube insertion part 321 can also be made small correspondingly.

Here, other forms of the locking part formed on the outer peripheral surface (outer wall 550) of the exterior tube insertion part 540 of the exterior tube 500 will be described.

In the exterior tube 500 of the above embodiment, for example if an irregular state of the exterior tube insertion part 540 of the exterior tube 500 is seen in the circumferential direction (the direction around the reference axis 500a) as illustrated in FIG. 15, the positions of the longitudinal grooves 504 serve as the recesses, and portions (portions where the lateral grooves 520 are formed) other than of the longitudinal groove 504 serve as the protrusions. As a result, these irregularities in the circumferential direction prevent the rotation of the exterior tube 500 around the reference axis 500a with respect to a body wall.

Figure 20:
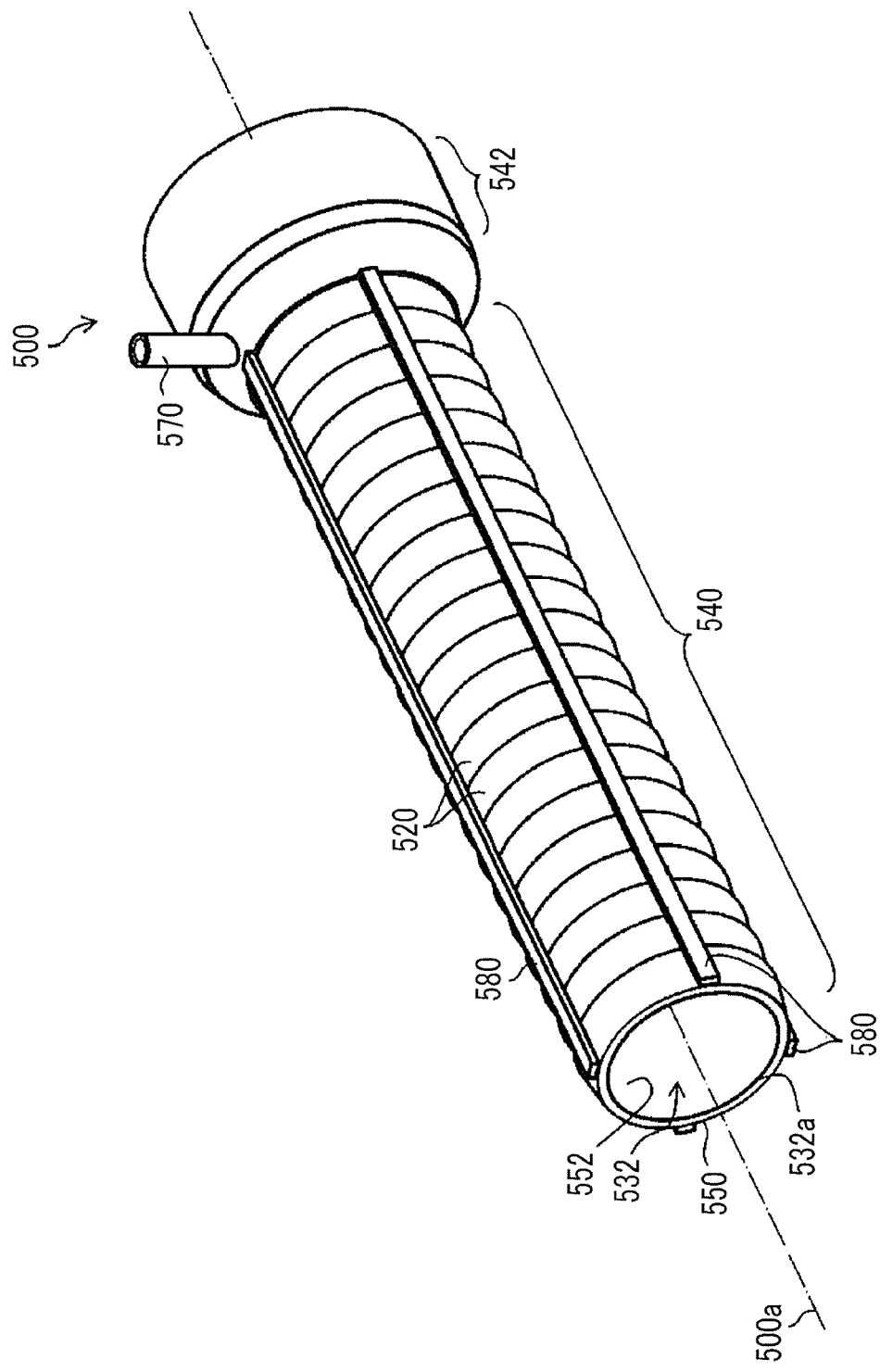
FIG. 20 is a perspective view illustrating another form of irregularities in an outer peripheral surface of the exterior tube.

In contrast, as illustrated in FIG. 20, protrusions 580 that in the direction of reference axis 500a may be formed instead of the longitudinal groove 504. The protrusions 580 are illustrated so as to protrude further radially outward than at least a bottom part (a portion with a smallest external diameter) of the lateral grooves 520. In the form of FIG. 20, although the protrusions 580 protrude further than portions where the external diameter of the lateral grooves 520 becomes the largest, the protrusions are not limited to this. In addition, in FIG. 20, the same reference signs will be given to constituent elements having functions the same as or similar to those of FIG. 15.

According to this, if the irregular state of the exterior tube insertion part 540 is seen in the circumferential direction and at different positions in the directions of reference axis 500a, in a case where the protrusions 580 protrude further radially outward than the portions (portions where the lateral grooves 520 are formed) other than the protrusions 580, the protrusions 580 serve as the protrusions and the other portions serve as the recesses. Meanwhile, in portions where the protrusions 580 are recessed further radially inward than the portions other than protrusions 580, the protrusions 580 serve as the recesses and the other portions serve as the protrusions. In the form of FIG. 20, in all the portions, the protrusions 580 serve as protrusions and the other portion serve as the recesses.

By virtue of such a form of the locking part, the rotation of the exterior tube 500 around the reference axis 500a with respect to a body wall can also be prevented.

In addition, a form in which the longitudinal grooves 504 as illustrated in FIG. 15 and the protrusions 580 as illustrated in FIG. 20 exist in a mixed manner may be adopted.

Next, other embodiments regarding the air supply mechanism for a pneumoperitoneum gas of the exterior tube 500 will be described.

Figure 21:
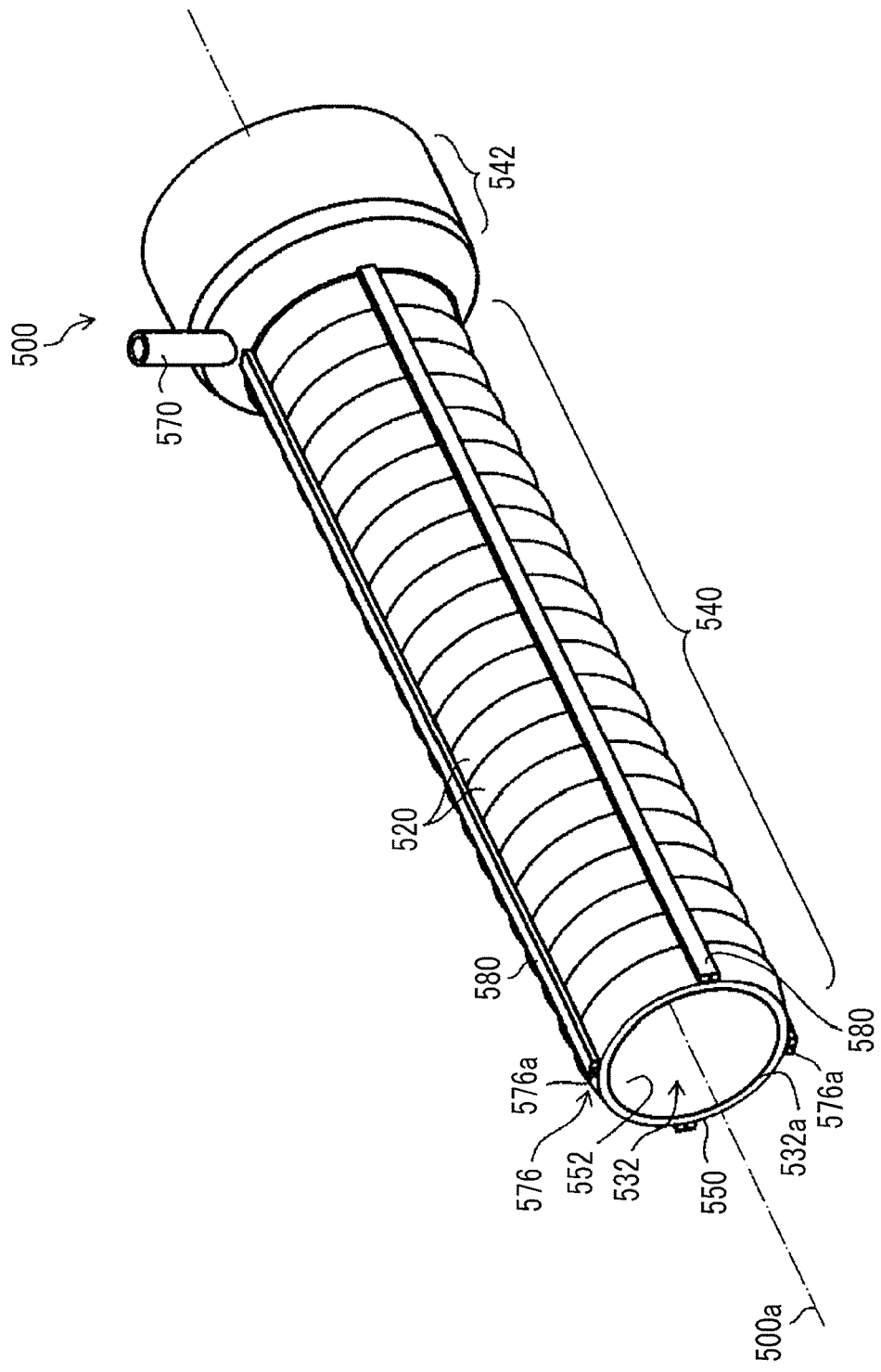
FIG. 21 is a perspective view of an exterior tube of another embodiment.
Figure 22:
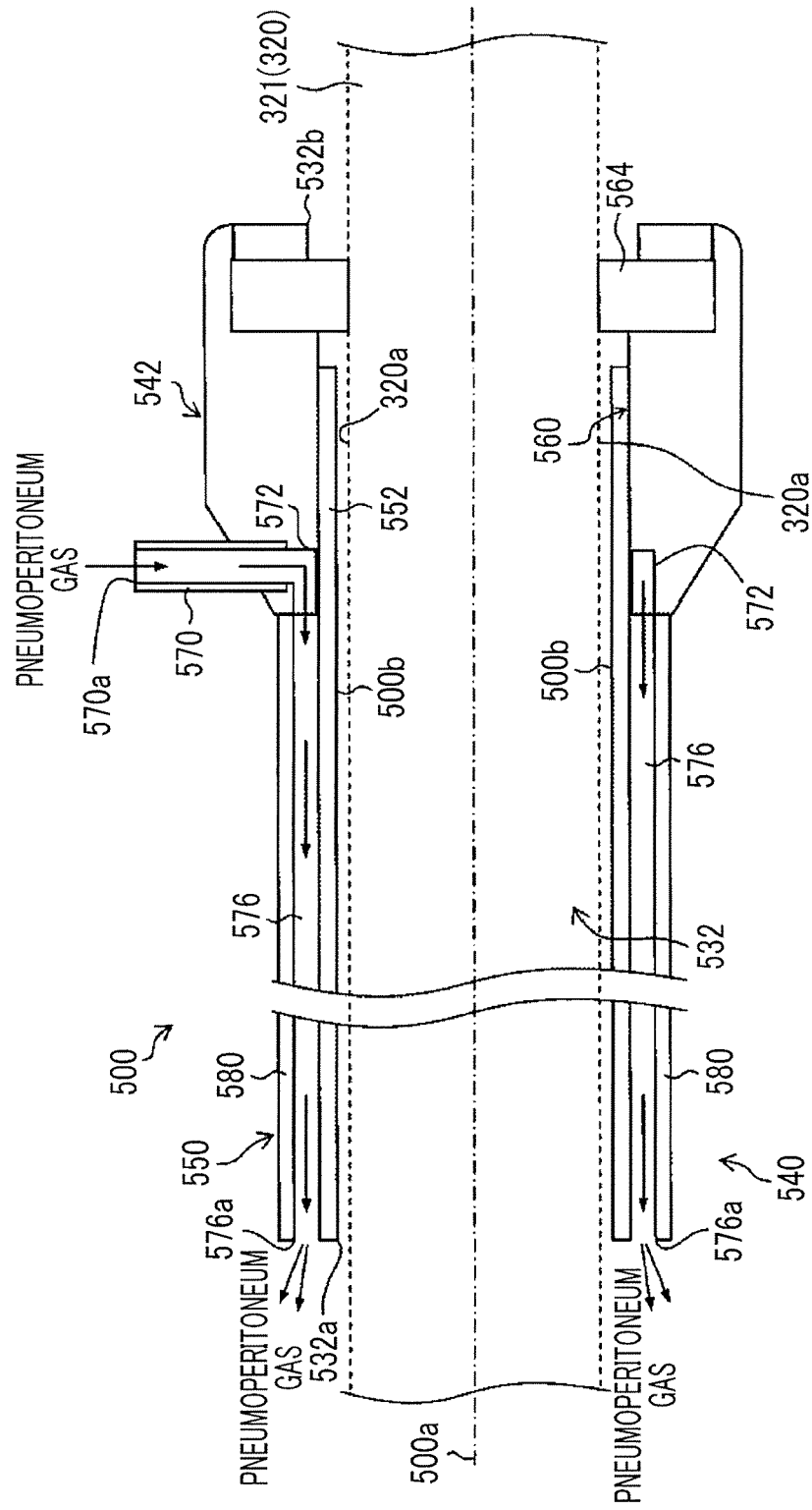
FIG. 22 is a cross sectional view illustrating a base end part and a distal end part in the exterior tube of the other embodiment of FIG. 21 in an enlarged manner.

FIG. 21 is a perspective view illustrating the external appearance of the exterior tube 500 of another embodiment, and FIG. 22 is an enlarged cross sectional view illustrating the base end part 542 and the distal end part of the exterior tube 500 of the other embodiment. In addition, in FIG. 21, the same reference signs will be given to constituent elements having functions the same as or similar to those of FIG. 20, in FIG. 22, the same reference signs will be given to constituent elements having functions the same as or similar to those of FIG. 19, and the detailed description thereof will be omitted.

As illustrated in FIG. 21, the lateral grooves 520 having completely the same form as the irregular shape illustrated in FIG. 21 and the protrusions 580 in the direction of the reference axis 500a are provided in the outer peripheral surface (outer wall 550) of the exterior tube insertion part 540 of the exterior tube 500 of the present embodiment.

Meanwhile, as illustrated in FIG. 22, an air supply passage 576 passing through each of the protrusions 580 in the direction of the reference axis 500a is formed in each of the protrusions 580 formed on the outer wall 550 of the exterior tube insertion part 540, and an air supply port 576a is formed at a distal end of the protrusion.

Figure 23:
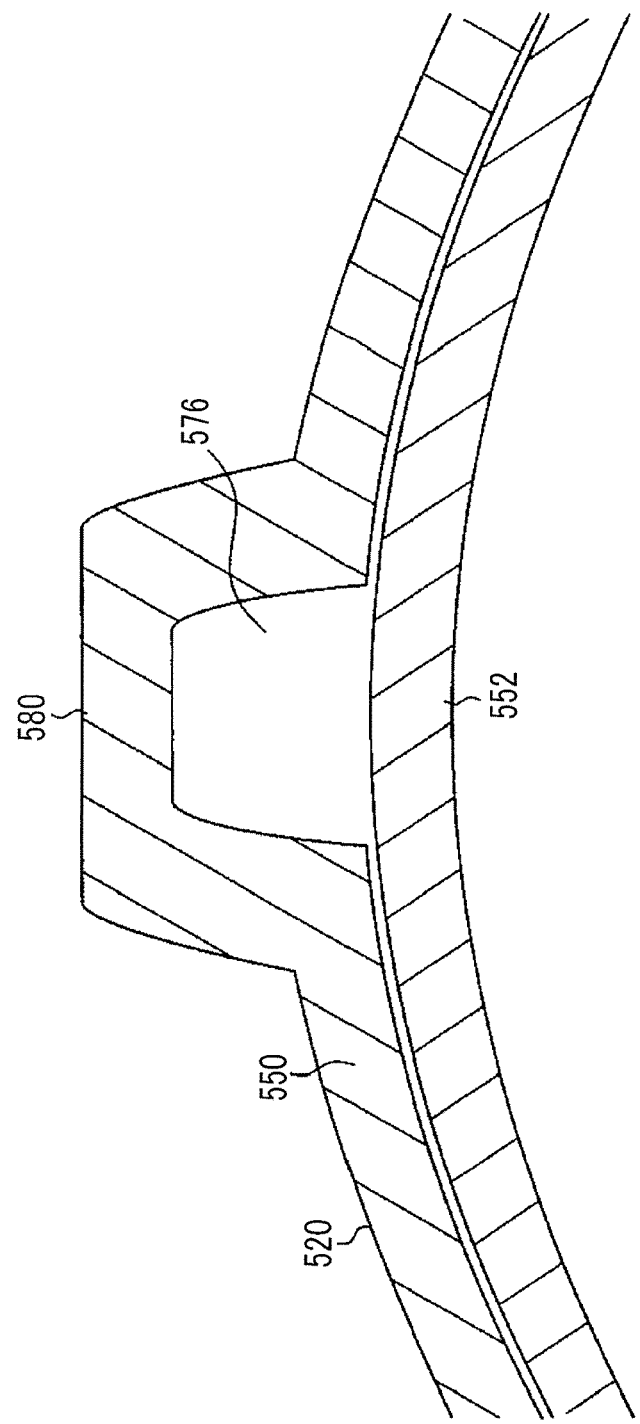
FIG. 23 is a cross sectional view around a protrusion in the exterior tube of the other embodiment of FIG. 21.

In addition, as illustrated in a cross sectional view of FIG. 23 in which the periphery of one protrusion 580 is cut in a plane perpendicular to the reference axis 500a, a groove is formed in the inner-peripheral-surface side of the outer wall 550 along with a protrusion 580, and a part for the opening that met in the direction of reference axis 500a of the groove is covered with the inner tube 552. Accordingly, the air supply passages 576 are formed inside the outer peripheral wall of the exterior tube insertion part 540.

However, the invention is not limited to this, and holes serving as the air supply passages 576 may be formed in the outer wall 550. Otherwise, as illustrated in FIG. 24, the air supply passages 576 may be provided by providing an air supply tube 582 that is a tube member independent from the exterior tube insertion part 540 along the reference axis 500a in contact with the outer peripheral surface of the exterior tube insertion part 540.

As illustrated in FIG. 22, an opening of each air supply passage 576 on the base end side communicates with the air supply passage 572 formed at the base end part 542 and is connected to the air supply connector 570 via the air supply passage 572. The air supply passage 572 extends in the circumferential direction, and is connected to the air supply passages 576 of all the protrusions 580 provided at equal intervals, for example, at positions of four places in the circumferential direction of the exterior tube insertion part 540.

If the working of the air supply mechanism for a pneumoperitoneum gas of the exterior tube 500 of the above-described other embodiment will be described and if the pneumoperitoneum gas is supplied to the air supply connector 570 via the air supply tube 122 from the pneumoperitoneum device 120 illustrated in FIG. 1, the pneumoperitoneum gas is sent to the air supply passage 576 in each of the protrusions 580 of the exterior tube insertion part 540 through the air supply passage 572 of the base end part 542 as illustrated in FIG. 22.

Then, the pneumoperitoneum gas sent to the air supply passages 576 flows through the air supply passages 576 toward the distal end side, and is delivered into a body cavity from the air supply ports 576a of the distal ends of the air supply passages 576 disposed at the distal end of the exterior tube 500.

Additionally, the protrusions 580 in which the air supply passages 576 are formed functions also as a locking part that prevents the rotation of the exterior tube 500 around the reference axis 500a with respect to the body wall as described above.

According to the air supply mechanism for a pneumoperitoneum gas in the above exterior tube 500, the air supply tube 122 to which the pneumoperitoneum gas from the pneumoperitoneum device 120 is supplied has only to be connected to the air supply connector 570 of the exterior tube 500. Therefore, it is easy to dispose the air supply tube 122, and the endoscope 100 and the treatment tool 200 inserted through the outer tube 300 in order to avoid contact therebetween. Therefore, any twist between the air supply tube 122 and the endoscope 100 or the treatment tool 200 can be prevented in advance without paying special attention.

Additionally, by adjusting the angle (or the angle of the outer tube 300 in the direction around the axis with respect to the exterior tube 500) of the exterior tube 500 in the direction around the axis with respect to the outer tube 300, the air supply connector 570 and the air supply tube 122 can be disposed in a body wall in a direction in which the endoscope 100 and the treatment tool 200 do not interfere with each other, regardless of the angular positions of the endoscope 100 and the treatment tool 200, inserted through the outer tube 300. Moreover, the angle of the outer tube 300 in the direction around the axis with respect to the exterior tube 500 can be set and changed to at arbitrary angles so as to bring about a state where the angular positions of the endoscope 100 and the treatment tool 200, inserted through the outer tube 300, in the direction around the axis is suitable for treatment, without the air supply tube 122 interfering with the endoscope 100 or the treatment tool 200.

Additionally, for example, compared to a case where a pneumoperitoneum gas is supplied through the endoscope insertion passage 306 and the treatment tool insertion passage 308 of the outer tube 300, regardless of the presence/absence of insertion of the endoscope 100 or the treatment tool 200 into the outer tube 300, air-supply flow rates in the air supply passages 572 and 576 can be substantially uniformly maintained, and stable supply of the pneumoperitoneum gas is possible.

Additionally, by making the protrusions 580 that form the air supply passages 576 of the exterior tube insertion part 540 of the exterior tube 500 serve also as the locking part that prevents the rotation of the exterior tube 500 around the reference axis 500a with respect to a body wall, the air supply passages 576 can be formed without causing an increase in the size (an increase in the diameter of the exterior tube insertion part 540) of the exterior tube.

In addition, the air supply passages 576 may be formed in all the protrusions 580 formed in the exterior tube insertion part 540, or may be formed in some protrusions 580. Additionally, the longitudinal grooves 504 illustrated in FIG. 15 may be formed instead of all or some protrusions 580 in which the air supply passages 576 are not formed.

Although a form in which the outer peripheral wall is configured such that the outer wall 550 and the base end part 542 of the exterior tube insertion part 540 are fixed to the outer peripheral part of the inner tube 552 is illustrated above as the exterior tube 500 of the above embodiment, the inner tube 552 and the outer wall 550 may be integrally formed. Additionally, the base end part 542 may not be fixed to the inner tube 552 if this base end has only to be connected to a base end of the exterior tube insertion part 540. Additionally, the base end part 542 of which the diameter is made larger than the exterior tube insertion part 540 may not be included.

Namely, the configuration of the exterior tube 500 may be any kind of configuration as long as the exterior tube 500 has an exterior tube main body having a base end, a distal end, and a longitudinal axis like the exterior tube insertion part 540 and the base end part 542 of the above embodiment and having an arbitrary structure, a distal end opening provided at the distal end of the exterior tube main body like the distal end opening 532a of the above embodiment, a base end opening provided at the base end of the exterior tube main body like the base end opening 532b of the above embodiment, an insertion passage that is provided along the longitudinal axis of the exterior tube main body, allows the distal end opening and the base end opening to communicate with each other, and has an outer tube inserted therethrough, like the insertion passage 532 of the above embodiment, a locking part that has a recess or protrusion formed along the longitudinal axis in an outer peripheral surface of the exterior tube main body and prevents the rotation of the exterior tube main body about the longitudinal axis, like the longitudinal grooves 504 or protrusions 580 of the above embodiment.

Additionally, the invention includes arbitrary surgical apparatuses for an endoscope having a supply port opening to the base end side of the exterior tube main body like the supply port 570a of the air supply connector 570 of the above embodiment, an air supply port opening to the distal end side of the exterior tube main body like the distal end opening 532a or an air supply port 576a of the above embodiment, and an air supply passage that is formed along the longitudinal axis of the exterior tube main body and allows the supply port and the air supply port communicate with each other, like the air supply passage 574 or an air supply passage 576 of the above embodiment.

Moreover, the invention includes not only the outer tube 300 of the above embodiment but also an outer tube that guides two arbitrary medical instruments into a body cavity, as the outer tube covered (sheathed) with the exterior tube.

That is, an outer tube that is inserted into a body cavity through a body wall and guides a first medical instrument having a first insertion part to be inserted into the body cavity and a second medical instrument having a second insertion part to inserted into the body cavity, into the body cavity is included. The endoscopes 100 and the endoscope insertion part 102 in the above embodiment are, for example, one form of the first medical instrument and the first insertion part, and the treatment tool 200 and the treatment tool insertion part 202 are one form of the second medical instrument and the second insertion part.

Additionally, as one form of the outer tube in this case, there is included an outer tube provided with an outer tube body having a distal end, a base end, and a longitudinal axis, a first distal end opening and a second distal end opening equivalent to the first distal end opening 312 and the second distal end opening 316 of the above embodiment that are provided at the distal end of the outer tube body, a first base end opening and a second base end opening equivalent to the first base end opening 310 and the second base end opening 314 of the above embodiment that are provided at the base end of the outer tube body, a first insertion passage equivalent to the endoscope insertion passage 306 of the above embodiment that is provided along the longitudinal axis of the outer tube body, allows the first distal end opening and the first base end opening to communicate with each other, and has a first insertion part inserted therethrough to be movable forward and backward, a second insertion passage equivalent to the treatment tool insertion passage 308 of the above embodiment that is provided along the longitudinal axis of the outer tube body, allows the second distal end opening and the second base end opening to communicate with each other, and has a second insertion part inserted therethrough to be movable forward and backward, and an interlocking member equivalent to the slider 400 of the above embodiment that has a first coupling part equivalent to the endoscope-coupling part 420 of the above embodiment to be coupled to the first insertion part inserted through the first insertion passage and a second coupling part equivalent to the treatment tool-coupling part 422 of the above embodiment to be coupled to the second insertion part inserted through the second insertion passage, and is movable forward and backward inside the outer tube body.

Moreover, the invention includes not only the exterior tube that guides the insertion parts of the two medical instruments into a body cavity but also an outer tube that guides one or three or more medical instruments into the body cavity, as the outer tube covered (sheathed) with the exterior tube.

EXPLANATION OF REFERENCES

10: surgical apparatus for endoscope
100: endoscope
102: endoscope insertion part
104: cable part
108: processor device
110: light source device
112: monitor
114: distal end surface
116: observation window
118: illumination window
120: pneumoperitoneum device
122: air supply tube
130: forward and backward movement operating part
132: hooking part
200: treatment tool
202: treatment tool insertion part
204: operating part
206: treatment part
300: outer tube
300a, 500a: reference axis
302: base end surface 306: endoscope insertion passage
306a: endoscope insertion axis
308: treatment tool insertion passage
308a: treatment tool insertion axis
310: first base end opening
312: first distal end opening
314: second base end opening
316: second distal end opening
320: long tubular outer tube body
320a: outer peripheral surface
321: outer tube insertion part
340: base end cap
360: distal end cap
400: slider
402: slider body
420: endoscope-coupling part
422: treatment tool-coupling part
426, 446: pressure-contact member
440: sleeve
444: sleeve body
500: exterior tube
500b: inner peripheral surface
504: longitudinal groove
520: lateral groove
522: side surface
524: tapered surface
532: insertion passage
532a: distal end opening
532b: base end opening
540: exterior tube insertion part
542: base end part
552: inner tube
564: airtight holding member
570: air supply connector
570a: supply port
572, 574, 576: air supply passage
576a: air supply port
580: protrusion
582: air supply tube

What is claimed is:

1. A surgical apparatus for an endoscope comprising:
an outer tube that guides an insertion part of a medical instrument into a body cavity, wherein the outer tube includes
an outer tube body having a distal end, a base end, and a longitudinal axis,
a first distal end opening and a second distal end opening provided at the distal end of the outer tube body,
a first base end opening and a second base end opening provided at the base end of the outer tube body,
a first insertion passage that is provided along the longitudinal axis of the outer tube body, and allows the first distal end opening and the first base end opening to communicate with each other and a first medical instrument to be inserted therethrough so as to be movable forward and backward,
a second insertion passage that is provided along the longitudinal axis of the outer tube body, allows the second distal end opening and the second base end opening to communicate with each other, and has a second medical instrument inserted therethrough to be movable forward and backward, and
an interlocking member that has a first coupling part to be coupled to the first medical instrument inserted through the first insertion passage and a second coupling part to be coupled to the second medical instrument inserted through the second insertion passage, and is movable forward and backward inside the outer tube body; and
an exterior tube, wherein the outer tube is sheathed within the exterior tube,
wherein the exterior tube includes
an exterior tube main body having a base end, a distal end, and a longitudinal axis,
a distal end opening provided at the distal end of the exterior tube main body,
a base end opening provided at the base end of the exterior tube main body,
an insertion passage that is provided along the longitudinal axis of the exterior tube main body, and allows the distal end opening and the base end opening to communicate with each other and the outer tube to be inserted therethrough,
a locking part that has a longitudinal recess or protrusion having a shape elongated along the longitudinal axis and formed along the longitudinal axis in an outer peripheral surface of the exterior tube main body and prevents a rotation of the exterior tube main body about the longitudinal axis, and
a supply port opening to a base end side of the exterior tube main body.

2. The surgical apparatus for an endoscope according to claim 1, further comprising
an airtight holding member that is provided inside the base end side of the exterior tube main body and holds airtightness in contact with the outer peripheral surface of the outer tube inserted through the insertion passage,
wherein the supply port is provided closer to a distal end side of the exterior tube main body than the airtight holding member with respect to the longitudinal axis of the exterior tube main body.

3. The surgical apparatus for an endoscope according to claim 1,
wherein the interlocking member has a non-sensing region where the forward and backward movement of any one of the first medical instrument and the second medical instrument does not interlock with the forward and backward movement of the other of the first medical instrument and the second medical instrument, and a sensing region where the forward and backward movement of any one of the first medical instrument and the second medical instrument interlocks with the forward and backward movement of the other of the first medical instrument and the second medical instrument.

* * * * *